United States Patent
Han et al.

(12)

(10) Patent No.: US 9,988,605 B2
(45) Date of Patent: Jun. 5, 2018

(54) METHOD FOR PREPARING ENDOCRINE AGGREGATE OF INSULIN-PRODUCING BETA CELLS FROM HUMAN PLURIPOTENT STEM CELLS

(71) Applicant: KOREA ADVANCED INSTITUTE OF SCIENCE AND TECHNOLOGY, Daejeon (KR)

(72) Inventors: Yong-mahn Han, Daejeon (KR); Young-jin Kim, Daejeon (KR); Hail Kim, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 448 days.

(21) Appl. No.: 14/453,799

(22) Filed: Aug. 7, 2014

(65) Prior Publication Data

US 2015/0159140 A1 Jun. 11, 2015

Related U.S. Application Data

(63) Continuation of application No. PCT/KR2013/011483, filed on Dec. 11, 2013.

(30) Foreign Application Priority Data

Dec. 11, 2013 (KR) .................. 10-2013-0153567

(51) Int. Cl.
*C12N 5/071* (2010.01)
*A61K 35/39* (2015.01)
*G01N 33/50* (2006.01)
*C07K 14/62* (2006.01)
*A61K 35/545* (2015.01)

(52) U.S. Cl.
CPC ............ *C12N 5/0677* (2013.01); *A61K 35/39* (2013.01); *G01N 33/507* (2013.01); *A61K 35/545* (2013.01); *C07K 14/62* (2013.01); *C12N 2500/12* (2013.01); *C12N 2500/38* (2013.01); *C12N 2501/01* (2013.01); *C12N 2501/115* (2013.01); *C12N 2501/15* (2013.01); *C12N 2501/155* (2013.01); *C12N 2501/16* (2013.01); *C12N 2501/335* (2013.01); *C12N 2501/385* (2013.01); *C12N 2501/41* (2013.01); *C12N 2501/415* (2013.01); *C12N 2501/727* (2013.01); *C12N 2506/02* (2013.01); *C12N 2506/45* (2013.01); *G01N 2500/10* (2013.01)

(58) Field of Classification Search
CPC .................................................. C12N 5/0677
See application file for complete search history.

(56) References Cited

U.S. PATENT DOCUMENTS

| 8,008,075 | B2* | 8/2011 | Green | C12N 5/0606 435/366 |
| 2007/0292388 | A1* | 12/2007 | Bouwens | C12N 5/0676 424/85.2 |
| 2010/0003757 | A1 | 1/2010 | Mack et al. | |
| 2010/0158868 | A1 | 6/2010 | Kan | |

FOREIGN PATENT DOCUMENTS

WO WO2003/050249 A2 6/2003

OTHER PUBLICATIONS

D'Amour et al., 2006, Nature Biotechnology, vol. 24(11), pp. 1392-1401.*
Zhang et al. "A Human iPSC Model of Hutchinson Gilford Progeria Reveals Vascular Smooth Muscle and Mesenchymal Stem Cell Defects." Cell Stem Cell 8, 31-45, Jan. 7, 2011.
Segev et al. "Differentiation of Human Embryonic Stem Cells into Insulin-Producing Clusters", Stem Cells, 2004; 22: 265-274.
Zhao, et al. "Two Supporting Factors Greatly Improve the Efficiency of Human iPSC Generation", Cell Stem Cell 3, Nov. 6, 2008, 475-479.

* cited by examiner

*Primary Examiner* — Thaian N Ton
*Assistant Examiner* — David A. Montanari
(74) *Attorney, Agent, or Firm* — Sheridan Ross P.C.

(57) ABSTRACT

The present invention prepared insulin-producing endocrine cells by inducing the differentiation of human embryonic stem cells or human induced pluripotent stem cells into definitive endoderm (DE), pancreatic endoderm (PE), endocrine progenitors (EP), and endocrine cells (EC) stepwise in that order. Particularly, the present invention established the conditions for the formation of an insulin producing endocrine aggregate (EA) from the endocrine cells. Especially in this invention, it was confirmed that the endocrine aggregate has the cell proliferation potential at a significant level and has the increased insulin productivity as well as the activity of inhibiting cell necrosis and apoptosis. Therefore, the method for preparing the endocrine aggregate of insulin-producing beta cells from human pluripotent stem cells can be effectively used for the examination of the medicinal effect of the conventional antidiabetic agents and of the novel antidiabetic drugs.

11 Claims, 29 Drawing Sheets

Fig.1a

| Stage 1 | Stage 2 | Stage 3 | Stage 4 | Stage 5 |
|---------|---------|---------|---------|---------|
| DE | PE | EP | EC | EA |
| CHIR + Li  Activin A | D5  DM + SB  Retionic Acid  ABK | D11  DM + SB  DAPT | D15  DM + SB  dbcAMP  Exendin-4  Nitoctinamide | D23  3D  Clustering  D26 |

Fig.1b

| | DE (Definitive Endoderm) | | PE (Pancreatic Endoderm) | EP (Endocrine progenitor) | EC (Endocrine Cells) | EA (Endocrine Aggregate) |
|---|---|---|---|---|---|---|
| Basal Media | DMEM/F12 | | DMEM | DMEM | | CMRL |
| Supplement | Day1 | Day2-S | 0.5x B27 | 0.5x B27 50 ug/ml ascorbic acid | 0.5x B27 50 ug/ml ascorbic acid 25 mM D-glucose | |
| | 0.2% BSA | 0.2% BSA + 0.5x B27 | | | | |
| Small molecules, Growth Factors | 50 ng/ml Activin A 3 uM CHIR99021 2 mM LiCl | | 2 uM RA 2 uM Dorsomorphin 10 uM SB431542 10 ng/ml Activin A 5 ng/ml bFGF 250 nM Kaad-cyclopamine | 2 uM Dorsomorphin 10 uM SB431542 10 uM DAPT (20 ng/ml HGF) | 500 uM dbcAMP 10 uM Exendin-4 2 uM Dorsomorphin 10 uM SB431542 10 mM Nicotinamide | |

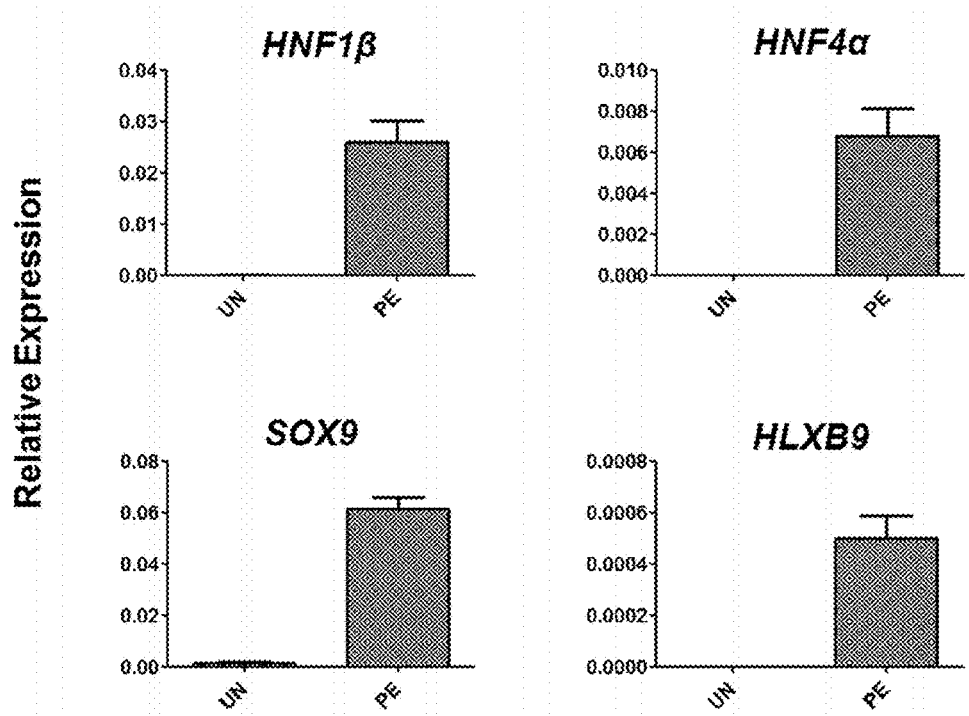

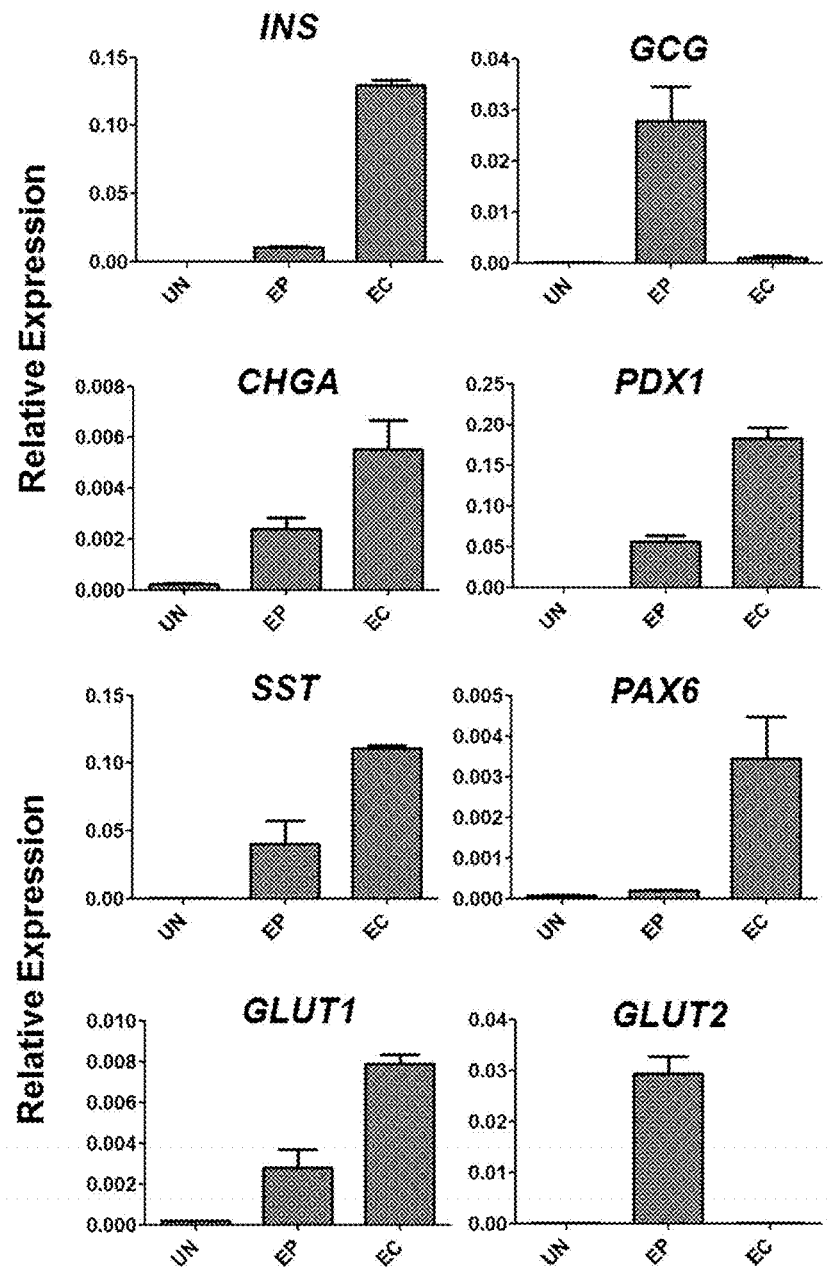

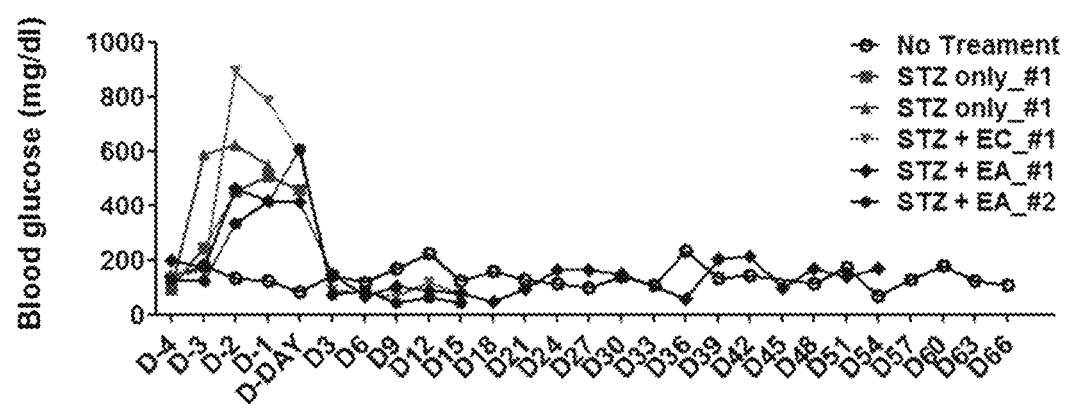

METHOD FOR PREPARING ENDOCRINE AGGREGATE OF INSULIN-PRODUCING BETA CELLS FROM HUMAN PLURIPOTENT STEM CELLS

CROSS REFERENCE TO RELATED APPLICATIONS

This application is a continuation application of International Application No. PCT/KR2013/011483, having an international filing date of Dec. 11, 2013, which PCT application claimed the benefit of Korean Application No. 10-2013-0153567 filed Dec. 11, 2013, the disclosures of each of which are incorporated herein by reference.

REFERENCE TO A SEQUENCE LISTING

This application contains a Sequence Listing submitted electronically as a text file. The text file, named "Seq_Listing.txt," has a size in bytes of 7 KB, and was created on Jul. 31, 2014. The information contained in the text file is incorporated herein by reference in its entirety pursuant to 37 CFR § 1.52(e)(5).

BACKGROUND OF THE INVENTION

1. Field of the Invention

The present invention relates to a method for preparing the endocrine aggregate (EA) of insulin-producing beta cells from human pluripotent stem cells (hPSCs).

2. Description of the Related Art

Stem cells are the cells in the phase right before the differentiation into each cell constructing each organ, which have self renewal capacity that makes unlimited proliferation in the non-differentiated state possible and have pluripotency, the ability to be differentiated into various tissues by a specific differentiation stimulus. That is, even after continued culture, self renewal capacity of the cells does not decrease and rather stays in order to make differentiation into various cells possible.

Stem cells are largely divided into two types, which are embryonic stem cells (ESCs) and adult stem cells (ASCs), according to the differentiation potential. When a sperm meets an egg, this leads to fertilization, followed by development and morphogenesis. At this time, the cells are through proliferation, migration, and differentiation processes. Embryonic stem cells are the cells separated from the inner cell mass (ICM) to be developed into a fetus, among the very beginning stage blastocyst embryos, before the fertilized egg is implanted in the endometrium, which are the pluripotent cells generated in three embryonic germ layers such as endoderm, ectoderm, and mesoderm to be differentiated into every cell to form every tissue.

In the meantime, adult stem cells are the organ specific stem cells obtained from the placenta in the stage of organ formation in the embryo under development or from an adult who has already been through all the cell development. The differentiation potency of these stem cells is limited in tissue specific cells, indicating that these cells are multipotent. Adult stem cells remain in most organs after all the differentiation to be grown up finishes in order to supplement any loss caused either normally or pathogenically. The representative adult stem cells are hematopoietic stem cells existing in the bone marrow and mesenchymal stem cells in the middle of differentiation into connective tissue except blood cells. Hematopoietic stem cells are differentiated into various blood cells including erythrocytes and leucocytes, while mesenchymal stem cells are differentiated into osteoblasts, chondroblasts, adipocytes, and myoblasts, etc.

Ever since the separation of human embryonic stem cells succeeded, the interest in their clinical application has been increased. Cell replacement therapy using stem cells as the perfect cell supplier has also been in the spotlight. Parkinson's disease, one of intractable diseases, neurodegenerative disease such as Alzheimer's disease, quadriplegia caused by spinal cord injury, leukemia, stroke, juvenile diabetes, myocardial infarction, and liver cirrhosis are such diseases that are caused by the destruction and permanent malfunction of tissue forming cells. Cell replacement therapy is the method to replace and supply cells for those diseases demonstrating the lack of cells.

Diabetes Mellitus is the disease that causes various acute/chronic complications and as a result it might cause various diseases and disorders in patients, resulting in early incompetence and even early death. This disease causes the increase of social medical costs and causes a deal of loss of labor, resulting in putting more burdens on the society overall. According to the World Health Report made by WHO in 1997, it is presumed that the number of diabetic patients is going to be increased to approximately 300 million in 2025. Especially, many developing countries in Asia and Africa will face diabetes epidemic carried by westernized way of life including diet. According to the epidemiologic study of diabetes in Korea, the prevalence rate of diabetes in Korean people at the age of over 30 s is presumed to be 8~9%, indicating the rate is rapidly increasing along with the modernization of society.

The treatment of diabetes mostly depends on insulin therapy. Oral hypoglycemic agent, insulin secretagogue, and insulin sensitizer are also used along with diet therapy and exercise therapy. However, modern medicine cannot cure the disease completely and transplantation of pancreatic islets might be the fundamental treatment, which though has problems of absolute lack of donors and side effects accompanied by the continuous administration of immunosuppressants.

The study on embryonic stem cells to treat diabetes has been actively going on, in which the study on the differentiation of pluripotent cells into insulin producing cells having the function of pancreatic β-cells stands in the middle. Lumelsky, et al. reported the differentiation of mouse embryonic stem cells into islet cells like insulin producing structure (Science 292:1389, 2001). Hori, et al. reported that when the insulin producing cells obtained from the mouse embryonic stem cells prepared by adding Pl-3 kinase suppressor were administered to the mouse diabetic model induced by streptozotocin, the insulin producing cells could regulate the high blood sugar level to the normal (PNAS 99:16105, 2002). In 1998, Thomson, et al. established human embryonic stem cells from the human blastula. Afterwards, the attempts have been actively made to obtain human insulin producing cells by differentiating the established human embryonic stem cells. However, it has been disclosed that human embryonic stem cells have unique stem cell characteristics and are very much different from mouse embryonic stem cells in their signal transduction system necessary for the cell differentiation into mature cells. As an attempt to prepare human insulin producing cells from human embryonic stem cells, Assady, et al. screened insulin producing cells by immunocytochemistry and enzyme-linked immunosorbent assay (ELISA) (Diabetes 50:1691, 2001). Later, the same research group reported that they succeeded in establishing insulin producing cells by taking advantage of the differentiation method proposed by Lumelsky, et al. (Stem Cells 22:265, 2004). However, the limitation in insulin production and secretion could not be overcome, yet.

Moreover, most insulin observed by immunocytochemistry in previous papers were the ones originated from culture media rather than biosynthesized in cells, that is cells absorbed insulin from the culture fluid during the culture and then later released it back to the medium by stimuli including high glucose level. Researchers even insisted that the insulin producing cells at this time were not healthy ones with experiencing apoptosis and many agreed with that (Sipione, et al., Diabetologia 47:499, 2004; Hansson, et al., Diabetes 53:2603, 2004; Rajagopal, et al., Science 299:363, 2003). Therefore, it is common understanding that the previous methods to produce insulin described in papers and patent documents have to be modified and further a novel method for inducing cell differentiation and identification thereof has to be studied. In particular, for the application to the clinical use, high purity insulin producing cells or cell clusters having normal functions have to be provided, asking continuous study to establish an efficient differentiation method. Considering the above, the patent technology retained by Geron Cooperation (10-2004-7008713, PCT/US2002/039089) has a weakness. That is, Geron Cooperation did not prove that the insulin observed by immunocytochemistry in the final product obtained by the patent technology was biosynthesized endogenously. Besides, no proof was included in that invention to explain whether or not the insulin therein was released out of the cells by an external glucose stimulus. In that patent technology, the differentiation was induced by using a cocktail comprising various differentiation factors having every possibility to affect the differentiation in their ways, but the analysis on such affection by those factors was not provided clearly.

In the course of study, to overcome the above problems, on the differentiation and proliferation mechanism of human embryonic stem cells into insulin producing beta cells, the present inventors succeeded in producing insulin secreting endocrine cells by inducing the differentiation of human embryonic stem cells or human induced pluripotent stem cells into definitive endoderm (DE), pancreatic endoderm (PE), endocrine progenitors (EP), and endocrine cells (EC) stepwise in that order. Particularly, the present inventors confirmed the conditions for the formation of the endocrine aggregate (EA) from the said endocrine cells, and confirmed that the said endogenous aggregate (EA) has the cell proliferation potential at a significant level, leading to the completion of this invention.

SUMMARY OF THE INVENTION

It is an object of the present invention to provide a method for preparing the endocrine aggregate (EA) of insulin-producing beta cells from human pluripotent stem cells, comprising the following steps:
1) differentiating human pluripotent stem cells (hPSCs) into insulin producing endocrine cells (EC); and
2) performing 3D clustering of the insulin producing endocrine cells differentiated in step 1) into the endocrine aggregate (EA).

It is another object of the present invention to provide the endocrine aggregate of insulin producing beta cells prepared by the above method.

It is also an object of the present invention to provide a method for promoting the proliferation of insulin producing cells which contains the step of culturing the endocrine aggregate of insulin producing beta cells.

It is further an object of the present invention to provide a method for the mass-production of insulin which contains the steps of culturing the endocrine aggregate of insulin producing beta cells and separating insulin from the culture product obtained thereby.

It is also an object of the present invention to provide a pharmaceutical composition for the treatment of diabetes containing the endocrine aggregate as an active ingredient.

It is also an object of the present invention to provide a method for screening antidiabetic drugs or a method for examining the effect of the same which contains the steps of treating the sample to the endocrine aggregate and analyzing the aggregate.

It is also an object of the present invention to provide a method for inducing insulin producing beta cells from human pluripotent stem cells comprising the following steps:
i) inducing the differentiation of human pluripotent stem cells (hPSCs) into definitive endoderm (DE);
ii) inducing the differentiation of the definitive endoderm (DE) of step i) into pancreatic endoderm (PE);
iii) inducing the differentiation of the pancreatic endoderm (PE) of step ii) into endocrine progenitors (EP); and
iv) inducing the differentiation of the endocrine progenitors (EPs) of step iii) into insulin producing endocrine cells (EC).

To achieve the above objects, the present invention provides a method for preparing the endocrine aggregate (EA) of insulin-producing beta cells from human pluripotent stem cells, comprising the following steps:
1) differentiating human pluripotent stem cells (hPSCs) into insulin producing endocrine cells (EC); and
2) performing 3D clustering of the insulin producing endocrine cells differentiated in step 1) into the endocrine aggregate (EA).

The present invention also provides the endocrine aggregate of insulin-producing beta cells prepared by the above method.

The present invention also provides a method for promoting the proliferation of insulin producing cells which contains the step of culturing the endocrine aggregate of insulin producing beta cells.

The present invention also provides a method for the mass-production of insulin comprising the following steps:
1) culturing the endocrine aggregate of insulin producing beta cells; and
2) separating insulin from the culture product obtained by the culture of step 1).

The present invention also provides a pharmaceutical composition for the treatment of diabetes containing the endocrine aggregate as an active ingredient.

The present invention also provides a method for screening antidiabetic drugs or a method for examining the effect of the same comprising the following steps:
1) treating the sample to the endocrine aggregate; and
2) analyzing the aggregate.

The present invention also provides a method for inducing insulin producing beta cells from human pluripotent stem cells comprising the following steps:
i) inducing the differentiation of human pluripotent stem cells (hPSCs) into definitive endoderm (DE);
ii) inducing the differentiation of the definitive endoderm (DE) of step i) into pancreatic endoderm (PE);
iii) inducing the differentiation of the pancreatic endoderm (PE) of step ii) into endocrine progenitors (EP); and iv) inducing the differentiation of the endocrine progenitors (EP) of step iii) into insulin producing endocrine cells (EC).

The present invention also provides a use of the endocrine aggregate of insulin producing beta cells prepared by the above method.

In addition, the present invention provides a use of the pharmaceutical composition for the treatment of diabetes comprising the endocrine aggregate as an active ingredient.

Advantageous Effect

In this invention, the differentiation from human embryonic stem cells or human induced pluripotent stem cells into definitive endoderm (DE), pancreatic endoderm (PE), endocrine progenitors (EP), and endocrine cells (EC) was induced stepwise in that order in order to form insulin producing endocrine cells. Particularly, the present inventors established in this invention the conditions for the formation of an insulin producing endocrine aggregate (EA) from the endocrine cells. Especially in this invention, it was confirmed that the endocrine aggregate has the cell proliferation potential at a significant level and the increased insulin productivity as well as the activity of inhibiting cell necrosis and apoptosis. Therefore, the present inventors provide a potential of the endocrine aggregate of insulin producing beta cells as a novel antidiabetic agent and usability of the same for the examination of the medicinal effect of the conventional antidiabetic agents.

BRIEF DESCRIPTION OF THE DRAWINGS

The application of the preferred embodiments of the present invention is best understood with reference to the accompanying drawings, wherein:

FIG. 1a is a diagram illustrating the steps of the differentiation of human embryonic stem cells (hESC) or human induced pluripotent stem cells (hiPSC) into insulin producing cells.

FIG. 1b is a diagram illustrating the culture fluids and compounds used in each step of the differentiation of human embryonic stem cells or human induced pluripotent stem cells into insulin producing cells.

FIG. 3d is a diagram illustrating the expressions of major transcription factors at mRNA level in pancreatic endoderm (PE) stage differentiated from human induced pluripotent stem cells.

FIG. 4c is a diagram illustrating the expressions of marker genes at molecular level through the differentiation of human embryonic stem cells into EP and EC.

FIG. 7a is a diagram illustrating that when the endocrine aggregate generated from insulin producing endocrine cells was transplanted in the mouse model with diabetes induced by the treatment of STZ, blood glucose was regulated over the time after the transplantation until the level reached normal blood glucose level.

DESCRIPTION OF THE PREFERRED EMBODIMENTS

Figure 2A:
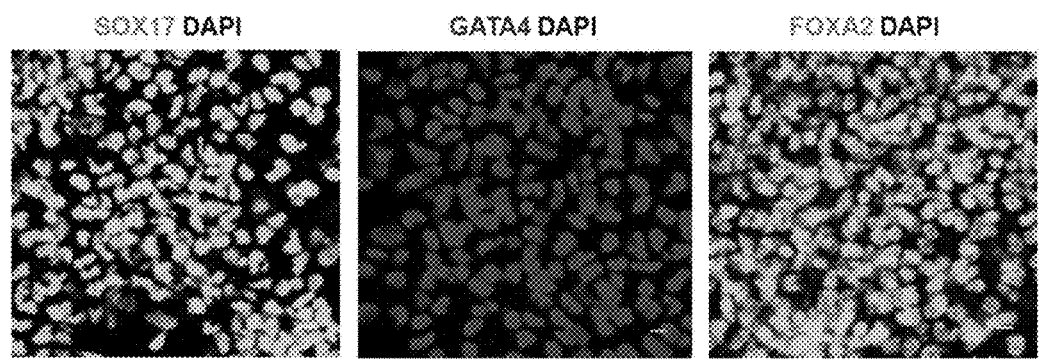
FIG. 2a is a diagram illustrating the expressions of major transcription factors at protein level in definitive endoderm (DE) stage, the first stage of the differentiation of human embryonic stem cells.

Hereinafter, the terms used in this invention are explained in detail.

The term "embryonic stem cells" in this invention indicates the pluripotent or totipotent cells that are able to be differentiated into every tissue cells, which are obtained from the inner cell mass extracted from blastocysts before implanted in uterus and by being cultured ex vivo. In a wide sense, embryoid bodies originated from embryonic stem cells are included. The said embryonic body is the interim structure formed by stem cells in the course of spontaneous differentiation into various tissues from embryonic stem cells, which is in the form of an aggregate generated in the course of embryonic stem cell culture. The embryonic stem cells in this invention can be originated from mammals including human and more preferably human embryonic stem cells.

The term "differentiation" in this invention indicates the phenomenon of specialization of cell structure or cell function during the proliferation of cells. Pluripotent embryonic stem cells are differentiated into limited progenitor cells (ex: ectodermal cells, mesodermal cells, or endodermal cells) first and then further differentiated into other types of progenitor cells such as hemangioblasts, etc, and lastly differentiated into fully differentiated cells such as vascular endothelial cells and vascular smooth muscle cells having a specific function in a specific organ (ex: blood vessels).

Hereinafter, the present invention is described in detail.

The present invention provides a method for preparing the endocrine aggregate (EA) of insulin-producing beta cells from human pluripotent stem cells (hPSCs), comprising the following steps:

1) differentiating human pluripotent stem cells (hPSCs) into insulin producing endocrine cells (EC); and
2) performing 3D clustering of the insulin producing endocrine cells differentiated in step 1) into the endocrine aggregate (EA).

In step 1), the said human pluripotent stem cells are preferably human embryonic stem cells (hPSCs) or human induced pluripotent stem cells (hiPSCs), but not always limited thereto.

The differentiating process of step 1) is composed of the following substeps:

a) inducing the differentiation of human pluripotent stem cells (hPSCs) into definitive endoderm (DE);
b) inducing the differentiation of the definitive endoderm (DE) of step a) into pancreatic endoderm (PE);
c) inducing the differentiation of the pancreatic endoderm (PE) of step b) into endocrine progenitors (EP); and
d) inducing the differentiation of the endocrine progenitors (EP) of step c) into insulin producing endocrine cells (EC).

In step a), it is preferred to induce the differentiation of human pluripotent stem cells (hPSCs) into definitive endoderm (DE) by culturing the cells in DMEM/F12 medium supplemented with Activin A, CHIR99021, and LiCl along with BSA or B27, but not always limited thereto.

The preferable concentrations of the said Activin A, CHIR99021, and LiCl were respectively 30~70 ng/ml, 2~4 μM and 1~3 mM, and more preferably 50 ng/ml, 3 μM, and 2 mM, but not always limited thereto.

The said BSA or B27 was preferably treated to the medium at the concentration of 0.1~0.3% (BSA) on day 1 of culture, 0.1~0.3% (BSA) and 0.3~0.7×B27 on day 2~day 5, and more preferably treated at the concentration of 0.2% BSA on day 1 and 0.2% BSA and 0.5×B27 on day 2~day 5, but not always limited thereto.

In step b), definitive endoderm (DE) was cultured in DMEM supplemented with RA (retinoic acid), dorsomorphin (DM), SB431542, Activin A, bFGF (basic fibroblast growth factor), and kaad-cyclopamine along with B27 in order to induce the differentiation of definitive endoderm (DE) into pancreatic endoderm (PE), but not always limited thereto.

The preferable concentrations of the said RA, dorsomorphin, SB431542, Activin A, bFGF, and kaad-cyclopamine were respectively 1~3 μM, 1~3 μM, 8~12 μM, 8~12 ng/ml, 4~6 ng/ml, and 220~270 nM, and more preferably 2 μM, 2 μM, 10 μM, 10 ng/ml, 5 ng/ml, and 250 nM, but not always limited thereto.

The said B27 was preferably 0.3~0.7×, and more preferably 0.5×, but not always limited thereto.

In step c), pancreatic endoderm (PE) was cultured in DMEM supplemented with dorsomorphin, SB431542, and DAPT treated with B27 and ascorbic acid in order to induce the differentiation of pancreatic endoderm (PE) into endocrine progenitors (EP), but not always limited thereto.

The preferable concentrations of the said dorsomorphin, SB431542, and DAPT were respectively 1~3 μM, 8~12 μM, and 8~12 μM, and more preferably 2 μM, 10 μM, and 10 μM, but not always limited thereto.

The preferable concentrations of the said B27 and ascorbic acid were respectively 0.3~0.7× and 30~70 μg/ml, and more preferably 0.5× and 50 μg/ml, but not always limited thereto.

In step d), endocrine progenitors (EP) was cultured in CMRL medium supplemented with dbcAMP, Exendin-4, dorsomorphin, SB431542, and nicotinamide along with B27, ascorbic acid, and D-glucose in order to induce the differentiation of endocrine progenitors (EP) into insulin producing endocrine cells (EC).

The preferable concentrations of the said dbcAMP, Exendin-4, dorsomorphin, SB431542, and nicotinamide were respectively 400~600 uM, 8~12 μM, 1~3 μM, 8~12 μM, and 8~12 mM, and more preferably 500 μM, 10 μM, 2 μM, 10 μM, and 10 mM, but not always limited thereto.

The preferable concentrations of the said B27, ascorbic acid, and D-glucose were respectively 0.3~0.7×, 40~60 μg/ml, and 20~30 mM, and more preferably 0.5×, 50 μg/ml, and 25 mM, but not always limited thereto.

The endocrine aggregate of step 2) can be compatible with the 3D cluster of endocrine cells. This endocrine aggregate has the growth possibility and the activity to increase the glucose transporter expression significantly.

The 3D clustering of step 2) was performed preferably by using the insulin producing endocrine cells in the middle of proliferation, and at this time, the preferable density of the insulin producing endocrine cells was $1\times10^4$~$1\times10^5$ cells, and more preferably $5\times10^4$ cells, but not always limited thereto.

In the 3D clustering of step 2), it was preferred that Y27632 was additionally treated in order to increase cell survival rate, but not always limited thereto.

The 3D clustering of step 2) was preferably performed for 20~28 hours, and more preferably for 22~26 hours, and most preferably for 24 hours, but not always limited thereto.

In a preferred embodiment of the present invention, to obtain insulin producing endocrine cells, human embryonic stem cells or human induced pluripotent stem cells were differentiated into definitive endoderm (DE), pancreatic endoderm (PE), endocrine progenitors (EP), and endocrine cells (EC) stepwise in that order. Then, an insulin producing endocrine aggregate was formed from the endocrine cells. Particularly, it was confirmed that the endocrine aggregate had the cell proliferation potential at a significant level and had the increased insulin productivity as well as the activity of inhibiting cell necrosis and apoptosis.

Therefore, the method for preparing the endocrine aggregate of insulin-producing beta cells of the present invention can be effectively used for the examination of the medicinal effect of the conventional antidiabetic agents and for the examination of the novel antidiabetic agent candidates.

The present invention also provides the endocrine aggregate of insulin-producing beta cells prepared by the above method.

It is preferred for the endocrine aggregate to respond against glucose or KCl in vitro to increase the secretion of C-peptide, the pro-insulin, but not always limited thereto.

The said aggregate is preferably composed of the cells in the middle of differentiation and the preferred density of the cells is $1\times10^4$~$1\times10^5$ cells, and more preferably $5\times10^4$ cells, but not always limited thereto.

The concentration of the said glucose is preferably 2.0~3.0 mM, and more preferably 2.3~2.9 mM, and most preferably 2.5 mM, but not always limited thereto.

It is preferred to treat KCl to the cells after treating glucose and the concentration of KCl is preferably 15~35 mM, and more preferably 30 mM, but not always limited thereto.

It is preferred for the endocrine aggregate to regulate homeostasis of glucose once it is transplanted in vivo, but not always limited thereto.

The amount of blood glucose is preferably 50~150 mg/dl, and more preferably 80~120 mg/dl, but not always limited thereto.

It was confirmed in this invention that the cluster having a specific function was formed from insulin producing endocrine cells within 24 hours after being finished with differentiation, which became the endocrine aggregate composed of insulin-producing beta cells. This aggregate was also confirmed to have an excellent activity to maintain homeostasis in vivo/in vitro, compared with endocrine cells before being differentiated into such an aggregate formed by responding to the stimulus of the high concentration of glucose or KCl, so that it can be effectively used for cell replacement therapy, for the examination of the medicinal effect of the conventional antidiabetic agents, and for the examination of the novel antidiabetic agent candidates.

The present invention also provides a method for promoting the proliferation of insulin producing cells which contains the step of culturing the endocrine aggregate of insulin-producing beta cells.

The said endocrine aggregate is composed of insulin expressing cells and characterized by the potential for proliferation.

The culture herein was preferably performed for 20~28 hours, and more preferably 22~26 hours, and most preferably 24 hours, but not always limited thereto.

The insulin producing cells are preferably insulin producing beta cells, but not always limited thereto.

The method for promoting the proliferation of insulin producing cells herein takes advantage of the said endocrine aggregate composed of insulin producing cells, which thus can be effectively used for the prevention and treatment of diabetes.

The present invention also provides a method for the mass-production of insulin comprising the following steps:
1) culturing the endocrine aggregate of insulin producing beta cells; and
2) separating insulin from the culture product obtained by the culture of step 1).

The method for the mass-production of insulin herein takes advantage of the said endocrine aggregate composed of insulin producing cells, which thus can be effectively used for the prevention and treatment of diabetes.

The present invention also provides a pharmaceutical composition for the treatment of diabetes containing the endocrine aggregate as an active ingredient.

The said diabetes is preferably type 2 diabetes, the non-insulin dependent diabetes mellitus, but not always limited thereto.

The pharmaceutically effective dosage of the composition of the present invention can be determined by considering various factors such as administration method, target area, patient condition, etc. Thus, the dosage for human body has to be determined with the consideration of safety and efficiency at the same time. It is also possible to predict the effective dosage based on the effective dosage confirmed by animal test. Various factors that have to be considered for the determination of the effective dosage are described in the following articles: Hardman and Limbird, eds., Goodman and Gilman's The Pharmacological Basis of Therapeutics, 10th ed. (2001), Pergamon Press; and E. W. Martin ed., Remington's Pharmaceutical Sciences, 18th ed. (1990), Mack Publishing Co.

The pharmaceutical composition of the present invention can include any generally used carrier, diluent, excipient, or a combination of at least two of those. The pharmaceutically acceptable carrier can be any carrier that is able to deliver the composition of the present invention in human body without limitation, which is exemplified by the compounds described in Merck Index, 13th ed., Merck & Co. Inc., such as saline, sterilized water, Ringer's solution, buffered saline, dextrose solution, maltodextrin solution, glycerol, ethanol, liposome and a mixture comprising one or more of those components. If necessary, a general additive such as antioxidant, buffer, and bacteriostatic agent can be additionally added. The composition of the present invention can be formulated in different forms including aqueous solutions, suspensions and emulsions for injection, pills, capsules, granules or tablets by mixing with diluents, dispersing agents, surfactants, binders and lubricants. The composition can further be prepared in suitable forms according to ingredients by following the method represented in Remington's Pharmaceutical Science (Mack Publishing Company, Easton Pa., 18th, 1990).

The pharmaceutical composition of the present invention can be administered orally or parenterally (for example, intravenous, hypodermic, peritoneal or local injection). The effective dosage of the composition can be determined according to weight, age, gender, health condition, diet, administration frequency, administration method, excretion and severity of a disease. The dosage is preferably 0.0001~10 mg/ml per day and more preferably 0.0001~5 mg/ml per day, and administration frequency is once a day or preferably a few times a day.

The present invention also provides a method for screening antidiabetic drugs or a method for examining the effect of the same comprising the following steps:
1) treating the sample to the endocrine aggregate; and
2) analyzing the aggregate.

The analysis herein is preferably performed to investigate the insulin secreting activity of the aggregate, the pro-insulin (C-peptide) secreting activity thereof, the blood glucose level, and also the cellular characteristics and the cell proliferation level, but not always limited thereto.

The said diabetes is preferably type 2 diabetes, the non-insulin dependent diabetes mellitus, but not always limited thereto.

The present invention also provides a method for inducing insulin producing beta cells from human pluripotent stem cells comprising the following steps:
i) inducing the differentiation of human pluripotent stem cells (hPSCs) into definitive endoderm (DE);
ii) inducing the differentiation of the definitive endoderm (DE) of step 1) into pancreatic endoderm (PE);
iii) inducing the differentiation of the pancreatic endoderm (PE) of step 2) into endocrine progenitors (EP); and
iv) inducing the differentiation of the endocrine progenitors (EPs) of step 3) into insulin producing endocrine cells (EC).

The present invention also provides a use of the endocrine aggregate of insulin producing beta cells prepared by the above method.

In addition, the present invention provides a use of the pharmaceutical composition for the treatment of diabetes comprising the endocrine aggregate as an active ingredient.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Inducement of the Differentiation of Human Pluripotent Stem Cells (hPSC) into Insulin Producing Beta Cells <1~1> Culture of Human Pluripotent Stem Cells Human embryonic stem cells and human induced pluripotent stem cells were used herein as human pluripotent stem cells. CHA15 human embryonic stem cells (hESCs) were donated from CHA Stem Cell Institute, Korea. HDF #1 human induced pluripotent stem cells (hiPSCs) were prepared by injecting and expressing OCT4, SOX2, KLF4, and c-MYC retrovirus in human dermal fibroblasts donated from Asan Medical Center, Seoul, Korea.

Particularly, the above two cell lines were cultured in stem cell culture media by using mitomycin-C (MMC) treated mouse embryonic fibroblasts as feeder cells. The composition of the human pluripotent stem cell culture medium was as follow: DMEM/F12, 20% knockout serum replacement, 1% penicillin-streptomycin (PenStrep), 1% nonessential amino acids (NEAA), 2 mM L-glutamate, 0.1 mM β-mercaptoethanol, and basic fibroblast growth factor (bFGF) (4 ng/ml for hESCs or 10 ng/ml for hiPSCs). All the components were purchased from Invitrogen (Carlsbad, Calif.). Human embryonic stem cells (hESCs) and human induced pluripotent stem cells (hiPSCs) were sub-cultured every 6 days, more precisely stem cell colonies were cut into 16~25 fragments by using 1 cc insulin syringe, which were treated with 10 mg/ml of collagenase IV (Gibco, Carlsbad, Calif.) for 4 minutes. Then, the fragments were taken off and transplanted in new feeder cell culture dishes.

<1~2> Inducement of the Differentiation of Human Pluripotent Stem Cells into Definitive Endoderm (DE)

The differentiation of human pluripotent stem cells into insulin producing endocrine cells was induced stepwise from definitive endoderm (DE) through pancreatic endoderm (PE), endocrine progenitors (EP), endocrine cells (EC) and endocrine aggregate (EA), the major secreting cells in the normal pancreas development (FIGS. 1a and 1b).

Particularly, to differentiate the human pluripotent stem cells of Example <1~1> into definitive endoderm (DE), the undifferentiated human embryonic stem cells (hESCs) or human induced pluripotent stem cells (hiPSCs) prepared in Example <1~1> were transplanted in the culture dish, followed by culture for 5 days. The culture dish contained DMEM/F12 as the basal medium which was supplemented with the following growth factors; 50 ng/ml of Activin A, 3 μM CHIR99021, and 2 mM LiCl, to which 0.2% BSA was added on day 1 of the culture and 0.2% BSA and 0.5×B27 were added on day 2~day 5.

<1~3> Inducement of the Differentiation of Definitive Endoderm (DE) into Pancreatic Endoderm (PE)

The definitive endoderm (DE) differentiated from human pluripotent stem cells in Example <1~2> was differentiated into pancreatic endoderm (PE).

Particularly, in order to differentiate the definitive endoderm (DE) prepared in Example <1~2> into pancreatic endoderm (PE), DMEM was used as the basal medium, to which following growth factors were added (2 μM RA, 2 μM dorsomorphin (DM), 10 μM SB431542, 10 ng/ml Activin A, 5 ng/ml bFGF, and 250 nM Kaad-cyclopamine), followed by culture for 6 days. 0.5×B27 was added to the culture for 6 days (day 5~day 11), starting 5 days after the differentiation of human pluripotent stem cells started, to induce the differentiation into pancreatic endoderm (PE).

<1~4> Inducement of the Differentiation of Pancreatic Endoderm (PE) into Endocrine Progenitors (EP)

The pancreatic endoderm (PE) differentiated from human pluripotent stem cells in Example <1~3> was differentiated further into endocrine progenitors (EP).

Particularly, in order to differentiate the pancreatic endoderm (PE) prepared in Example <1~3> into endocrine progenitors (EP), DMEM was used as the basal medium, to which following growth factors were added [2 μM dorsomorphin (DM), 10 μM SB431542, and 10 μM DAPT (20 ng/ml HGF)], followed by culture for 4 days. 0.5×B27 and 50 μg/ml ascorbic acid were added to the medium for 4 days (day 11~day 15), starting days after the first differentiation of human pluripotent stem cells started, to induce the differentiation into insulin producing endocrine progenitors (EP).

<1-5> Inducement of the Differentiation of Endocrine Progenitors (EP) into Endocrine Cells (EC)

The insulin producing endocrine progenitors (EP) differentiated from human pluripotent stem cells in Example <1-4> were differentiated into insulin producing endocrine cells (EC).

Particularly, in order to differentiate the pancreatic endocrine progenitors (EP) prepared in Example <1-4> into endocrine cells (EC), CMRL was used as the basal medium, to which following growth factors were added (500 µM dbcAMP, 10 µM Exendin-4, 2 µM dorsomorphin, 10 µM SB431542, and 10 mM nicotinamide), followed by culture for 4 days. 0.5×B27, 50 µg/ml ascorbic acid, and 25 mM D-glucose were added to the medium for 8 days (day 15~day 23), after the first differentiation of human pluripotent stem cells started, to induce the differentiation into pancreatic endocrine cells.

Example 2: Confirmation of the Differentiation into Insulin Producing Definitive Endoderm (DE)

<2-1> Confirmation of the Expressions of SOX17, GATA4, and FOXA2 in Definitive Endoderm To confirm the insulin producing definitive endoderm differentiated from human pluripotent stem cells in Example <1-2> in the molecular level, the expressions of such proteins as SOX17, GATA4, and FOXA2 in the definitive endoderm were examined by immunostaining.

Particularly, insulin producing definitive endoderm cells were prepared by differentiating by the same manner as described in Example <1-2> the human embryonic stem cells and human induced pluripotent stem cells cultured by the same manner as described in Example <1-1>. Then, the prepared definitive endoderm cells were treated with 4% formaldehyde, followed by fixing at room temperature for 30 minutes. The cells were washed with PBS containing 0.1% Tween 20 (PBST) three times, 10 minutes each, and then treated with PBS containing 0.1% triton X-100 for 30 minutes to give permeability to cell membrane. The treated cells were treated with 1% bovine serum albumin, followed by blocking at room temperature for 1 hour. The cells were treated then with the primary antibody, anti-SOX17 goat antibody (1:200, product #: AF1924; R & D, USA), anti-GATA4 mouse antibody (1:200, product #: sc-25310; Santa Cruz, USA), or anti-FOXA2 Rabbit antibody (1:200, product #: 3143S; Cell Signaling, USA), followed by culture at 4° C. for overnight. Then, the cells were washed with PBST 5 times. After washing, the cells were treated with the secondary antibody, Alexa Fluor 488 or Alexa Fluor 594 conjugated donkey originated secondary antibody (1:1000; Invitrogen, USA), followed by culture for 1 hour, by which SOX17, GATA4, and FOXA2 proteins in definitive endoderm were immunostained. To compare the expressions of those proteins, nuclei of the cells were stained with 4'6-diamidino-2-phenylindole (DAPI), which were then observed under fluorescence microscope (Olympus, Japan) or Zeiss LSM 510 confocal microscope (Carl Zeiss, Germany). The expressions of the proteins, SOX2 and NCAD, were confirmed.

Figure 2B:
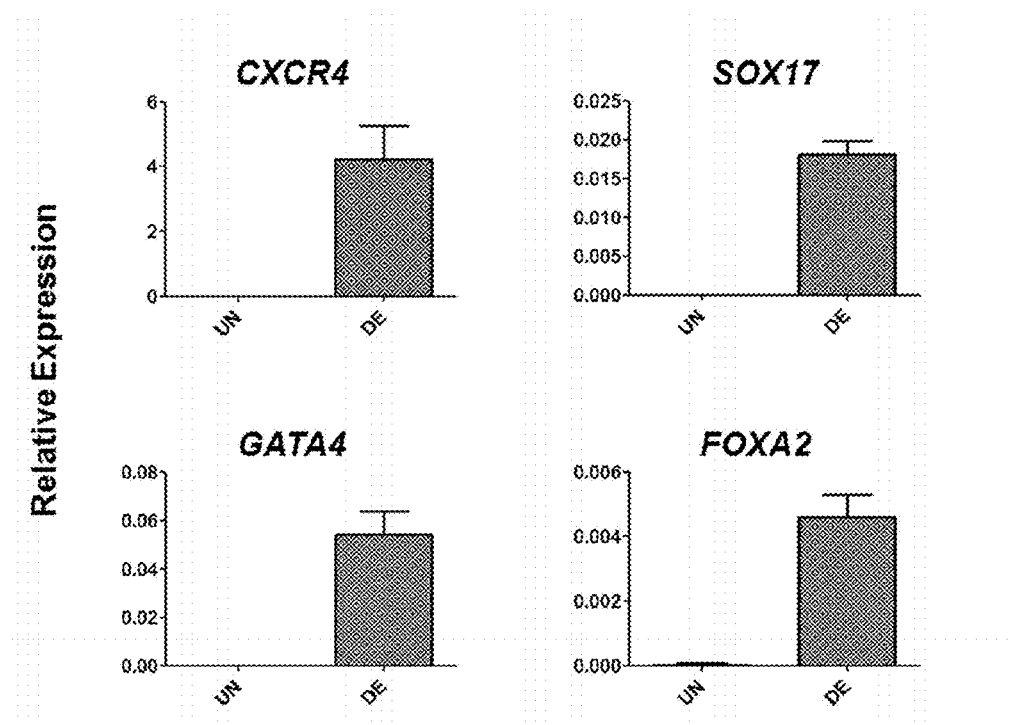
FIG. 2b is a diagram illustrating the expressions of major transcription factors at mRNA level in definitive endoderm (DE) stage differentiated from human embryonic stem cells.
Figure 2C:
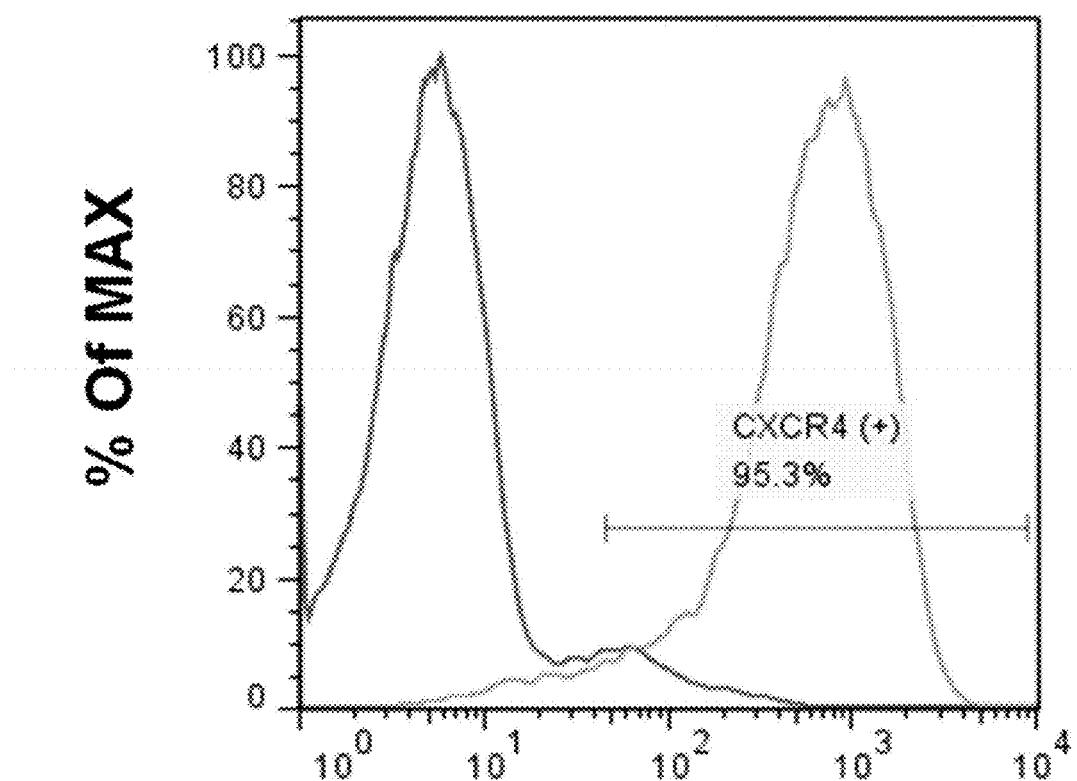
FIG. 2c is a diagram illustrating that at least 95% cells were differentiated from human embryonic stem cells into definitive endoderm (DE), confirmed by surface marker FACS.
Figure 2D:
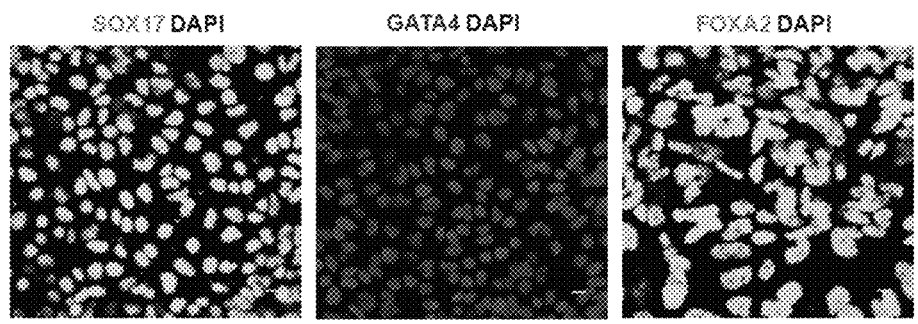
FIG. 2d is a diagram illustrating the expressions of major transcription factors at protein level in definitive endoderm (DE) stage differentiated from human induced pluripotent stem cells.

As a result, as shown in FIGS. 2a and 2d, after inducing the differentiation of human embryonic stem cells into definitive endoderm (DE), the first differentiation stage, the major transcription factors playing an important role in definitive endoderm stage, SOX17, GATA4, and FOXA2, were all expressed significantly (FIG. 2a and FIG. 2d).

<2-2> Confirmation of the Expressions of CXCR4, SOX17, GATA4, and FOXA2 in Definitive Endoderm To confirm the insulin producing definitive endoderm differentiated from human pluripotent stem cells in Example <1-2> in the molecular level, the transcriptional expressions of the definitive endoderm specific markers CXCR4, SOX17, GATA4, and FOXA2 mRNAs in the definitive endoderm were examined by RT-PCR (reverse transcription polymerase chain reaction).

Particularly, insulin producing definitive endoderm cells were prepared by differentiating by the same manner as described in Example <1-2> the human embryonic stem cells and human induced pluripotent stem cells cultured by the same manner as described in Example <1-1>. Total RNA was extracted from the prepared cells by using Ribo EX (GeneAll, Korea). 1 µg of the extracted RNA was used as a template and M-mlV reverse transcriptase (Enzynomics, USA) and the primers shown in Table 1 were used for the synthesis of cDNA of each CXCR4, SOX17, GATA4, and FOXA2. The primers shown in Table 1 were mixed with 2×q PCR premix at the concentration of 5 pmol, followed by real-time PCR with iCycler iQ5 real-time detection system (Bio-Rad laboratories, USA) under the conditions described in Table 2. The expressions of CXCR4, SOX17, GATA4, and FOXA2 in definitive endoderm were confirmed and compared. As the control to calibrate the expression levels above, the expression of GAPDH gene was confirmed by the same manner as described above.

TABLE 1

Primer sequences for the confirmation of the transcriptional expressions of the definitive endoerm specific markers

| Target Gene | SEQ ID. NO | Primer | Primer Sequence | Length (bp) |
| --- | --- | --- | --- | --- |
| CXCR4 | SEQ. ID. NO: 1 | CXCR4_F | ggtggtctatgttggcgtct | 227 |
|  | SEQ. ID. NO: 2 | CXCR4_R | tggagtgtgacagcttggag |  |
| SOX17 | SEQ. ID. NO: 3 | SOX17_F | cagaatccagacctgcacaa | 154 |
|  | SEQ. ID. NO: 4 | SOX17_R | gcggccggtacttgtagtt |  |
| GATA4 | SEQ. ID. NO: 5 | GATA4_F | tccaaaccagaaaacggaag | 187 |
|  | SEQ. ID. NO: 6 | GATA4_R | ctgtgcccgtagtgagatga |  |
| FOXA2 | SEQ. ID. NO: 7 | FOXA2_F | aacaagatgctgacgctgag | 126 |
|  | SEQ. ID. NO: 8 | FOXA2_R | caggaaacagtcgttgaagg |  |

TABLE 2

Conditions for real-time PCR

| Temperature | Time | Repeat |
|---|---|---|
| 95° C. | 10 min. | |
| 95° C. | 30 sec. | 40 |
| 60° C. | 30 sec. | |
| 72° C. | 30 sec. | |
| 72° C. | 5 min. | |

Figure 2E:
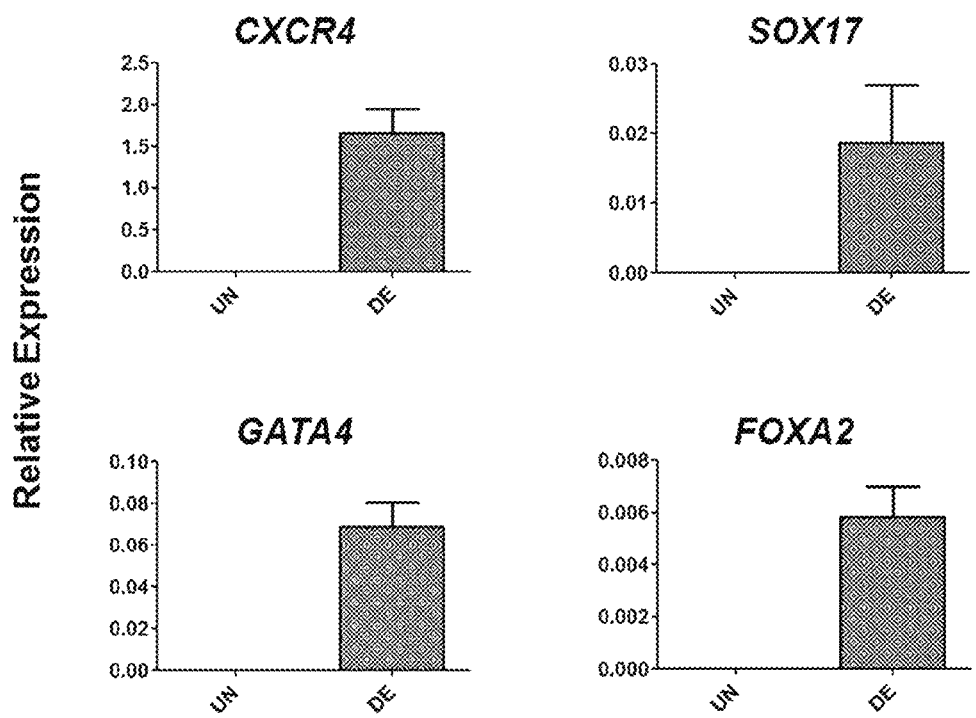
FIG. 2e is a diagram illustrating the expressions of major transcription factors at mRNA level in definitive endoderm (DE) stage differentiated from human induced pluripotent stem cells.

As a result, as shown in FIGS. 2b and 2e, the definitive endoderm specific markers, CXCR4, SOX17, GATA4, and FOXA2, were not expressed in human embryonic stem cells, but the expressions were confirmed comparatively high in the differentiated definitive endoderm at mRNA level. (FIGS. 2b and 2e).

Example 3: Confirmation of the Differentiation into Insulin Producing Pancreatic Endoderm (PE)

To confirm the insulin producing pancreatic endoderm differentiated from human pluripotent stem cells in Example <1-3> in the molecular level, immunostaining and RT-PCR were performed.

Particularly, insulin producing pancreatic endoderm cells were prepared by differentiating human embryonic stem cells and human induced pluripotent stem cells by the same manner as described in Example <1-3>. Immunostaining was performed with the major marker protein PDX1 using anti-PDX1 rabbit antibody (1:1000, product #: ab47267; Abcam, USA) by the same manner as described in Example <2-1>, followed by examination of the expression thereof. The transcriptional expressions of PDX1, HNF1β, HNF4α, HLXB9, and SOX9 mRNAs in pancreatic endoderm were confirmed by using the primers listed in Table 3 by the same manner as described in Example <2-2>.

TABLE 3

Primer sequences for the confirmation of the transcriptional expressions of pancreatic endoderm specific expressions

| Target Gene | SEQ ID. NO | Primer | Primer Sequence | Length (bp) |
|---|---|---|---|---|
| PDX1 | SEQ. ID. NO: 9 | PDX1_F | GTTCCGAGGTAGAGGCTGTG | 250 |
| | SEQ. ID. NO: 10 | PDX1_R | AACATAACCCGAGCACAAGG | |
| HNF1 | SEQ. ID. NO: 11 | HNF1_F | AGCCCACCAACAAGAAGATG | 145 |
| | SEQ. ID. NO: 12 | HNF1_R | CATTCTGCCCTGTTGCATCC | |
| HNF4 | SEQ. ID. NO: 13 | HNF4_F | CGAGCAGATCCAGTTCATCA | 149 |
| | SEQ. ID. NO: 14 | HNF4_R | CGTTGGTTCCCATATGTTCC | |
| SOX9 | SEQ. ID. NO: 15 | SOX9_F | TACGACTACACCGACCACCA | 213 |
| | SEQ. ID. NO: 16 | SOX9_R | TCAAGGTCGAGTGAGCTGTG | |
| HLXB9 | SEQ. ID. NO: 17 | HLXB9_F | GCACCAGTTCAAGCTCAACA | 133 |
| | SEQ. ID. NO: 18 | HLXB9_R | CTTTTTGCTGCGTTTCCATT | |

<2-3> Confirmation of the Expression of CXCR4 in Definitive Endoderm

To confirm the insulin producing definitive endoderm differentiated from human pluripotent stem cells in Example <1-2> molecular genetically, FACS (fluorescence-activated cell sorting) was performed using the definitive endoderm surface marker.

Particularly insulin producing definitive endoderm cells were prepared by differentiating by the same manner as described in Example <1-2> the human embryonic stem cells and human induced pluripotent stem cells cultured by the same manner as described in Example <1-1>. The prepared cells were treated with Accutase (Innovative Cell Technologies, USA), followed by culture at 37° C. for 10 minutes. Then, the cells were treated with allophycocyanin (APC) mouse anti-human CD184 (CXCR4) Fluorescence-Activated Cell Sorting antibody (BD Biosciences, USA), followed by further culture. Flow cytometry analysis was performed using BD FACS. For the isotype control, flow cytometry analysis was performed using the definitive endoderm surface marker and APC mouse IgG2a k isotype antibody (BD Biosciences, USA) by the same manner as described above.

Figure 2F:
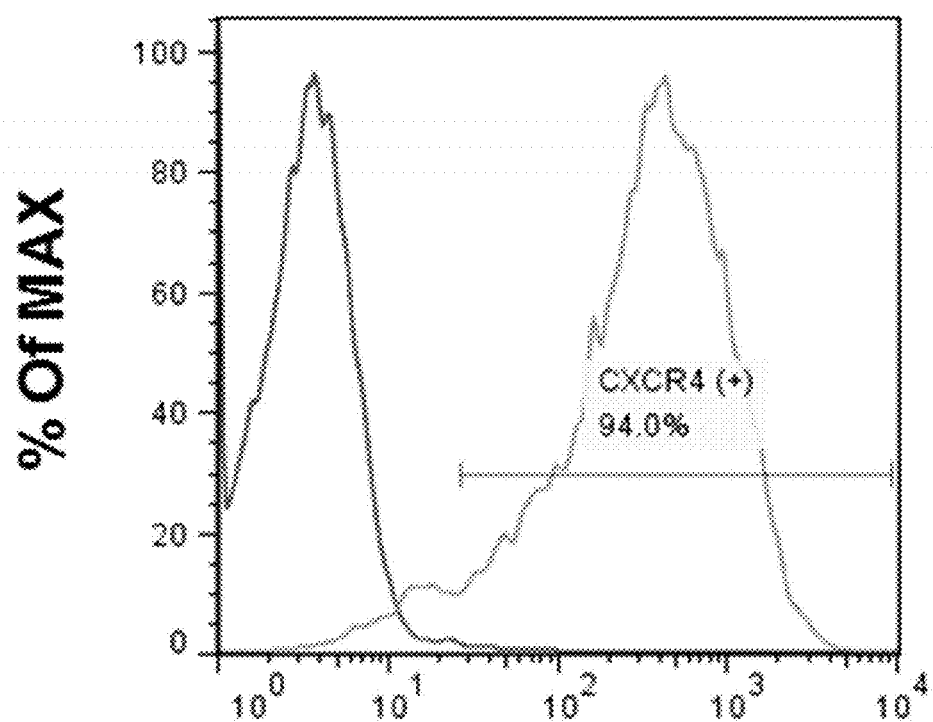
FIG. 2f is a diagram illustrating that at least 94% cells were differentiated from human induced pluripotent stem cells into definitive endoderm (DE), confirmed by surface marker FACS.

As a result, as shown in FIGS. 2c and 2f, it was confirmed that at least 95% of the cells were differentiated into definitive endoderm (FIGS. 2c and 2f).

Figure 3A:
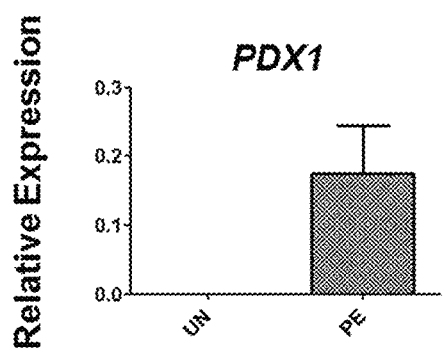
FIG. 3a is a diagram illustrating the expressions of the representative transcription factor both at protein and mRNA level in pancreatic endoderm (PE) stage differentiated from human embryonic stem cells.
Figure 3A:
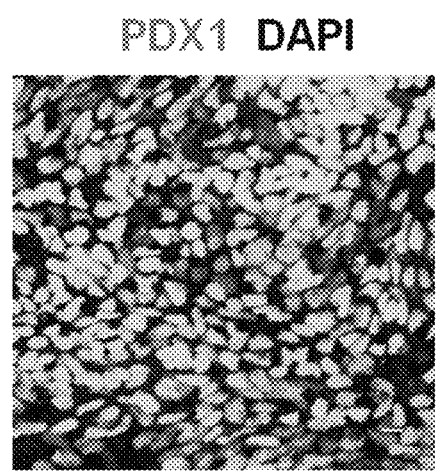
Figure 3B:
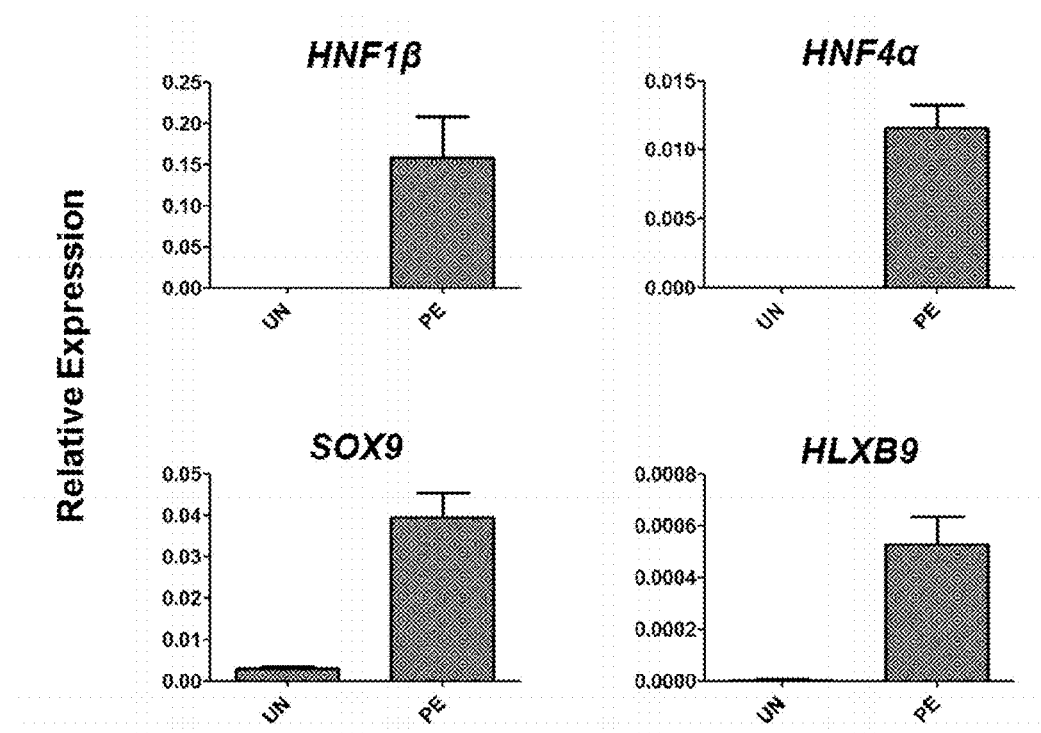
FIG. 3b is a diagram illustrating the expressions of major transcription factors at mRNA level in pancreatic endoderm (PE) stage differentiated from human embryonic stem cells.
Figure 3C:
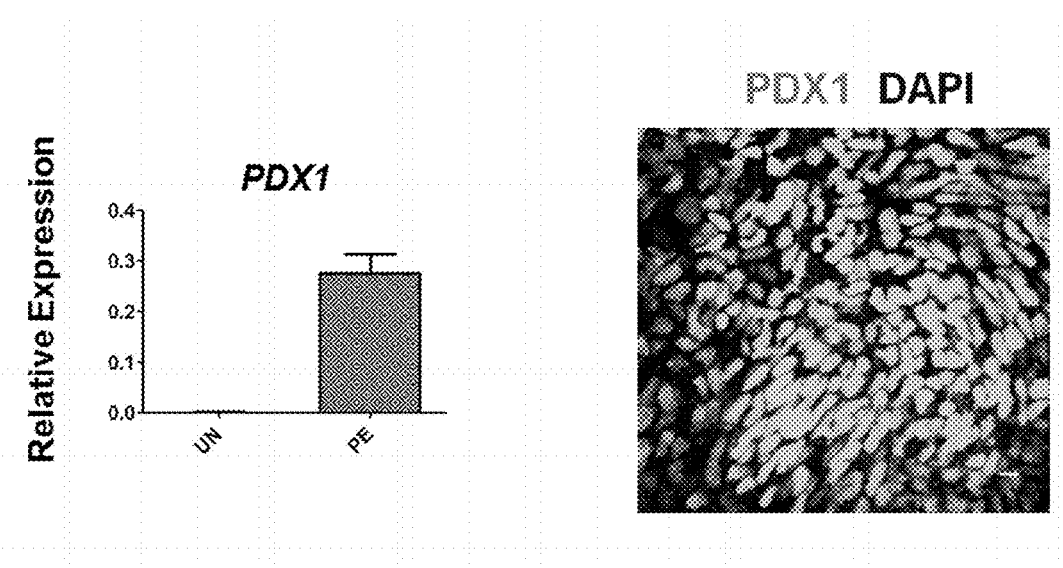
FIG. 3c is a diagram illustrating the expressions of the representative transcription factor both at protein and mRNA level in pancreatic endoderm (PE) stage differentiated from human induced pluripotent stem cells.

As a result, as shown in FIG. 3a and FIG. 3c, which illustrates the result of immunostaining to investigate the differentiation of definitive endoderm differentiated from human embryonic stem cells and human induced pluripotent stem cells into pancreatic endoderm, it was confirmed that the major transcription factor PDX1 was significantly expressed in pancreatic endoderm (FIGS. 3a and 3c).

The expressions of the PE markers, HNF1β, HNF4α, HLXB9, and SOX9, were also investigated at mRNA levels. As a result, compared with human embryonic stem cells and human induced pluripotent stem cells, the expressions of those markers were significantly high in pancreatic endoderm (FIGS. 3b and 3d).

Example 4: Confirmation of the Differentiation into Insulin Producing Endocrine Cells (EC)

To confirm the insulin producing endocrine cells differentiated from human pluripotent stem cells through insulin producing endocrine progenitors in Example <1-4> in the molecular level, immunostaining and RT-PCR were performed with those endocrine cells.

Particularly, insulin producing endocrine cells differentiated from human embryonic stem cells and human induced pluripotent stem cells were prepared by the same manner as described in Example <1-4>. Immunostaining was performed with the endocrine hormone marker insulin (INS), glucagon (GCG), somatostatin (SST), A-amylase, C-peptide, and chromagranin A by using the antibodies shown in Table 4 by the same manner as described in Example <2-1> to confirm the expressions thereof.

The transcriptional expressions of INS, GCG, SST, PDX1, CHGA, and GLUT1 in the endocrine cells were also investigated by using the primers shown in Table 5 by the same manner as described in Example <2-2>.

TABLE 4

Primary antibodies for the confirmation of the expressions of endocrine cell hormone markers

| Antibody | Origin | Dilution | Production company | Product # |
|---|---|---|---|---|
| Anti-insulin antibody | Guinea pig | 1:500 | Dako, Japan | A056401 |
| Anti-C-peptide antibody | Mouse | 1:500 | Abcam, USA | ab8297 |
| Anti-glucagon antibody | Mouse | 1:1000 | Sigma, USA | G2654 |
| Anti-somatostatin antibody | Rabbit | 1:1000 | Dako, Japan | A0566 |
| Anti-A-amylase antibody | Rabbit | 1:100 | Sigma, USA | A8273 |
| Anti-chromagranin antibody | Mouse | 1:200 | Millipore, USA | MAB 5268 | which as differentiation progressed, insulin was up-regulated but glucagon (GCG), the antagonist of insulin, was down-regulated. The expressions of other genes therein were similar to the normal in vivo development procedure (FIGS. 4c and 4d).

Example 5: Inducement and Confirmation of the Endocrine Aggregate from Insulin Producing Endocrine Cells <5-1> Inducement of the Endocrine Aggregate from Insulin Producing Endocrine Cells Differentiated from Human Embryonic Stem Cells The insulin producing endocrine cells whose differentiation was confirmed at protein and mRNA levels in Example 4 were dropped into single cells to form the endocrine aggregate.

Figure 5A:
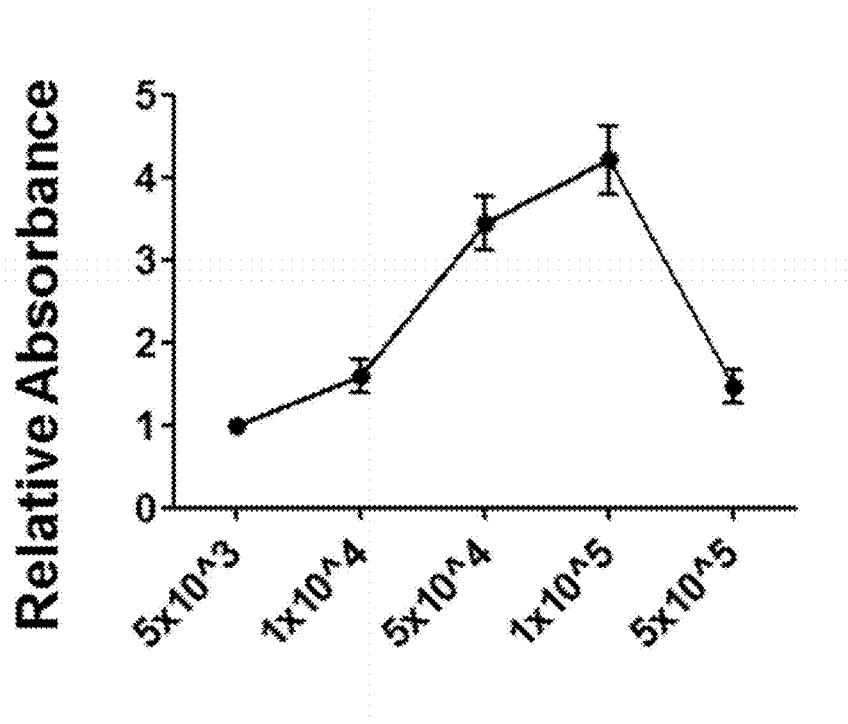
FIG. 5a is a diagram illustrating the cell viability in the cource of endocrine aggregate (EA) formation, for which the differentiated cells obtained in monolayer culture were dropped into single cells.

Particularly, to form the endocrine aggregate, the cells in the middle of cell proliferation were inoculated in the non-treated 96 well plate at the seeding density of $5 \times 10^4$ as shown in FIG. 5A. To enhance viability of the single cells, 300×Y27632 (A.G scientific, USA) was treated at the concentration of 1/300 (total volume), followed by inducing the formation of the endocrine aggregate. Then, the endocrine aggregate was collected and then INS and C-peptide were immunostained with the antibodies listed in Table 4 by the same manner as described in Example <2-1>, followed by the examination of insulin expression.

TABLE 5

Primer sequences for the confirmation of the transcriptional expressions of endocrine cell hormone markers

| Target Gene | SEQ ID. NO | Primer | Primer Sequence | Length (bp) |
|---|---|---|---|---|
| INS | SEQ. ID. NO: 19 | INS_F | CCAGCCGCAGCCTTTGTGA | 343 |
|  | SEQ. ID. NO: 20 | INS_R | GGTTCAAGGGCTTTATTCCATCT |  |
| GCG | SEQ. ID. NO: 21 | GCG_F | AGGCAGACCCACTCAGTGA | 308 |
|  | SEQ. ID. NO: 22 | GCG_R | AACAATGGCGACCTCTTCTG |  |
| SST | SEQ. ID. NO: 23 | SST_F | CCCCAGACTCCGTCAGTTTC | 108 |
|  | SEQ. ID. NO: 24 | SST_R | TCCGTCTGGTTGGGTTCAG |  |
| CHGA | SEQ. ID. NO: 25 | CHGA_F | CCTGTCAGCCAGGAATGTTT | 235 |
|  | SEQ. ID. NO: 26 | CHGA_R | CATCCTTGGATGATGGCTCT |  |
| PAX6 | SEQ. ID. NO: 27 | PAX6_F | TGTGTGCTCTGAAGGTCAGG | 170 |
|  | SEQ. ID. NO: 28 | PAX6_R | CTGGAGCTCTGTTTGGAAGG |  |
| GLUT1 | SEQ. ID. NO: 29 | GLUT1_F | GCAACGGCTTAGACTTCGAC | 283 |
|  | SEQ. ID. NO: 30 | GLUT1_R | TGCGACTTCAGGCACATAAC |  |
| KI67 | SEQ. ID. NO: 31 | KI67_F | CTTTGGGTGCGACTTGACG | 199 |
|  | SEQ. ID. NO: 32 | KI67_R | GTCGACCCCGCTCCTTTT |  |

Figure 4A:
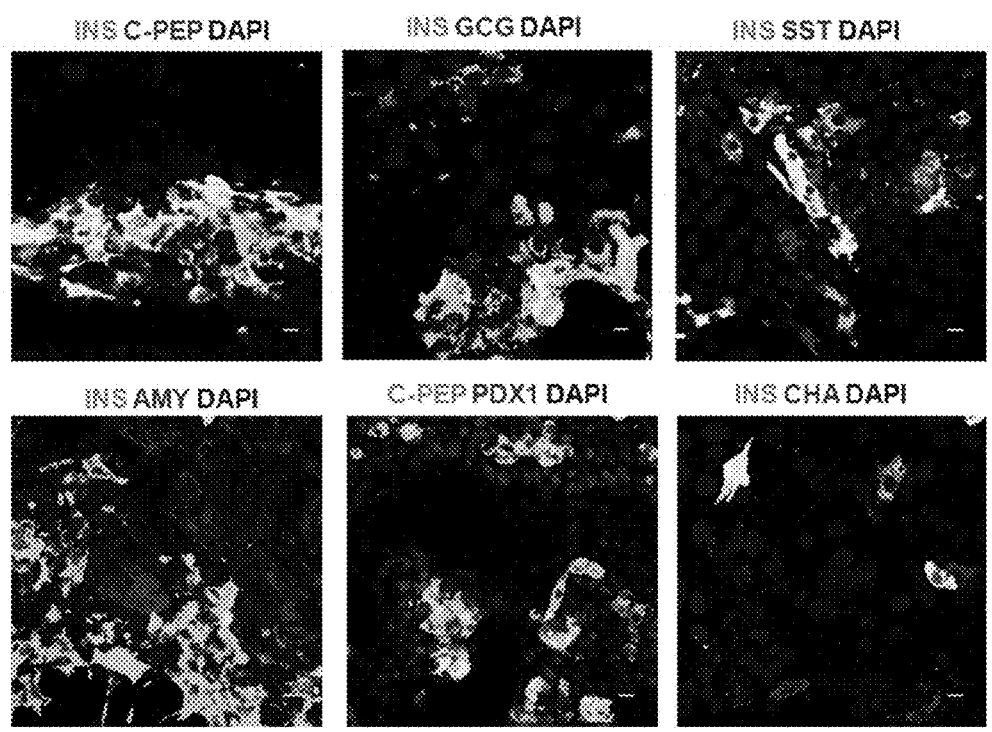
FIG. 4a is a diagram illustrating that the differentiation of human embryonic stem cells into endocrine cells (EC) in monolayer was confirmed at protein level by using not only insulin secreted in pancreas but also other hormones such as glucagon (GCG) and somatostatin (SST) as markers.
Figure 4B:
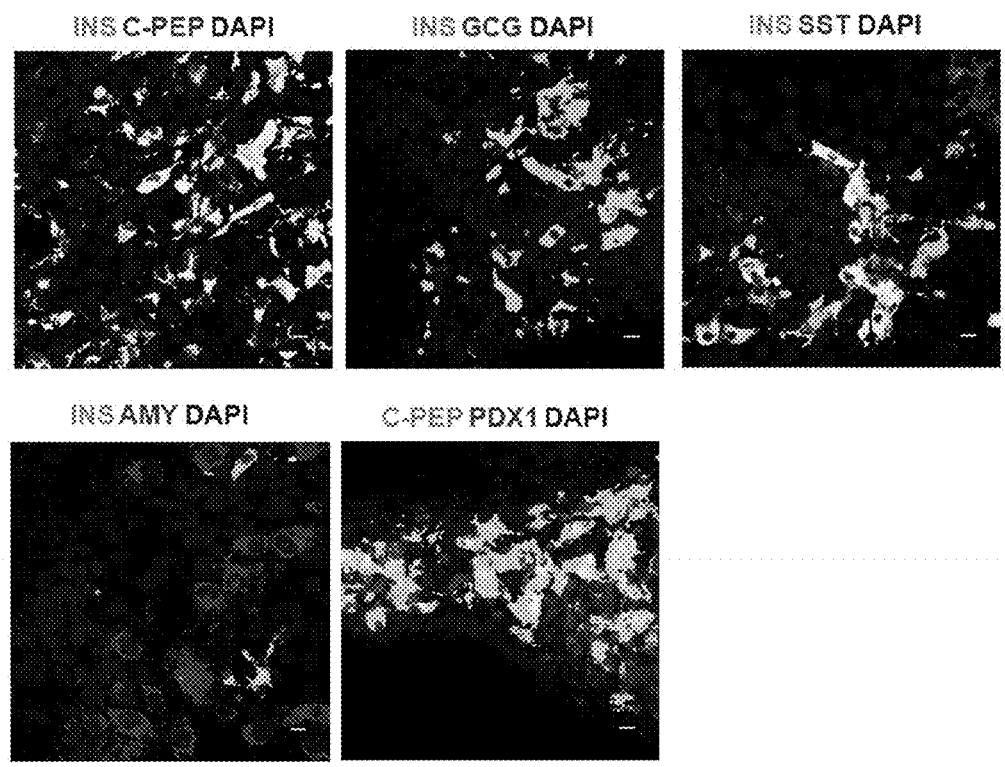
FIG. 4b is a diagram illustrating that the differentiation of human induced pluripotent stem cells into endocrine cells was confirmed at protein level by using each endocrine hormone as a marker.
Figure 4D:
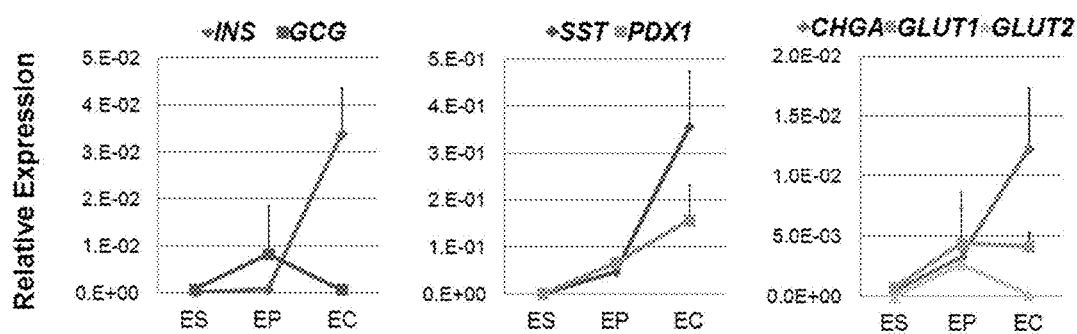
FIG. 4d is a diagram illustrating the expressions of marker genes at molecular level through the differentiation of human induced pluripotent stem cells.

As shown in FIG. 4a and FIG. 4b, the expressions of endocrine hormone markers in the monolayer of the endocrine cells differentiated from human embryonic stem cells and human induced pluripotent stem cells were investigated. As a result, not only the expression of insulin, the hormone secreted in pancreas, but also the expressions of other endocrine hormones such as somatostatin (SST) and chromogranin A (CHA) were significantly increased (FIGS. 4a and 4b).

Figure 5B:
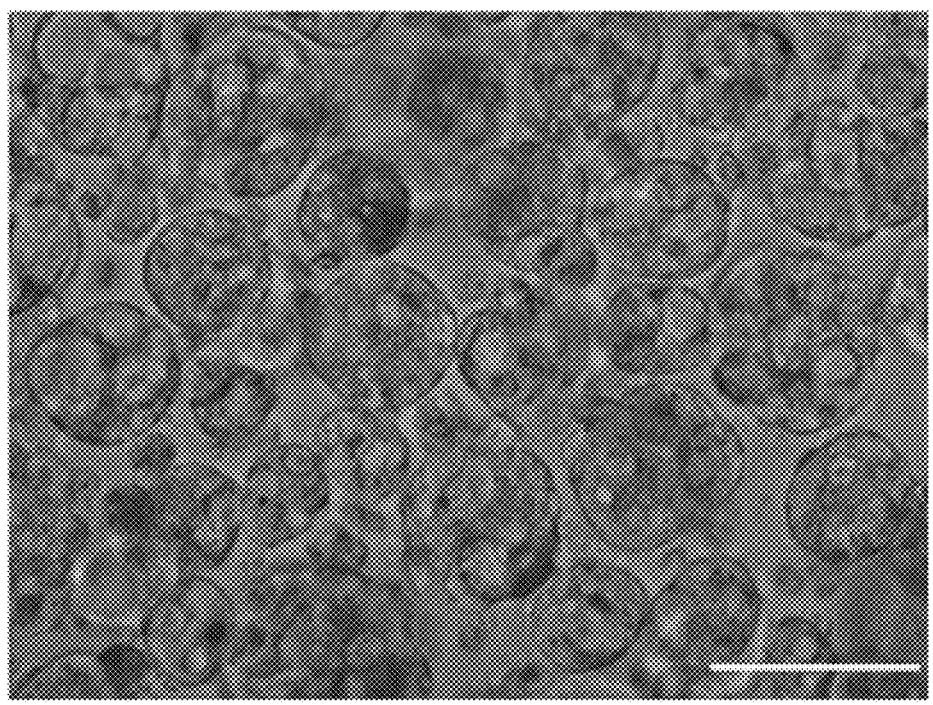
FIG. 5b is a diagram illustrating the endocrine aggregate generated from human embryonic stem cell-derived endocrine cells which was activated 24 hours later.
Figure 5C:
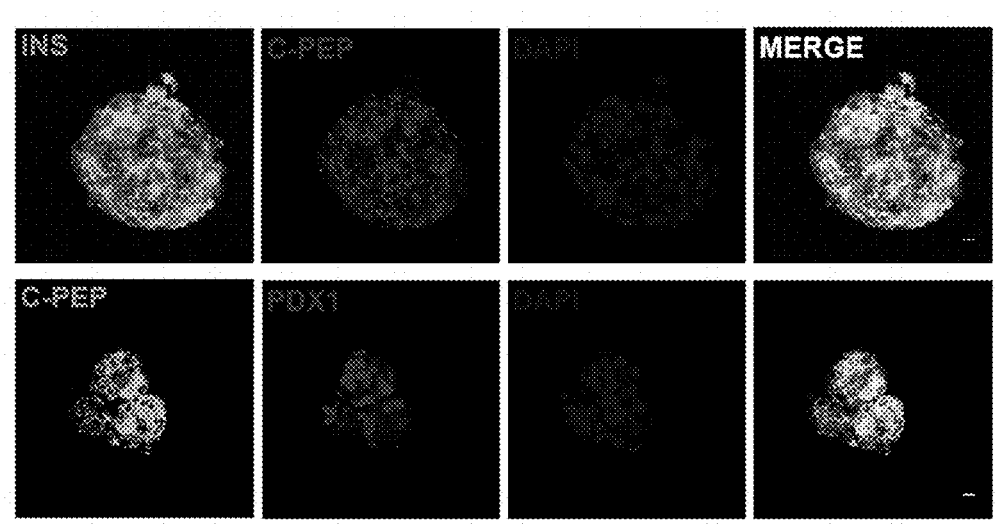
FIG. 5c is a diagram illustrating that the endocrine aggregate was largely composed of insulin expressing cells differentiated from human embryonic stem cells and particularly expressed beta cell specific markers.

FIG. 4c illustrates the mRNA expressions of those marker genes in endocrine cells originated from human embryonic stem cells and human induced pluripotent stem cells, As shown in FIG. 5a and FIG. 5b, the cell differentiation over the seeding density, induced during the formation of the endocrine aggregate from the insulin producing endocrine cells (single cells) differentiated from human embryonic stem cells, was observed. As a result, the cells were most proliferated and formed into the endocrine aggregate best at the seeding density of $5 \times 10^4$ (FIG. 5a). The endocrine aggregate formed from human embryonic stem cells was activated 24 hours later (FIG. 5b). The endocrine aggregate generated from human embryonic stem cells expressed the beta cell specific marker most selectively, and was confirmed to be composed mostly of insulin expressing cells (FIG. 5c).

<5-2> Confirmation of the Growth Possibility of the Endocrine Aggregate Generated from Insulin Producing Endocrine Cells Originated from Human Embryonic Stem Cells To investigate whether the endocrine aggregate could be proliferated or not, the expressions of K167 and GLUT1, the proliferation indexes, were investigated in the endocrine aggregate.

Particularly, the endocrine aggregate formed in Example <5-1> was obtained. The transcriptional expressions of INS, GCG, K167, and GLUT1 mRNAs were investigated by the same manner as described in Example <2-2>. To compare the expression levels, the transcriptional expression level of insulin mRNA in the endocrine cells differentiated in Example <1-4> was first confirmed, based on which the comparative expression levels were measured.

Figure 5D:
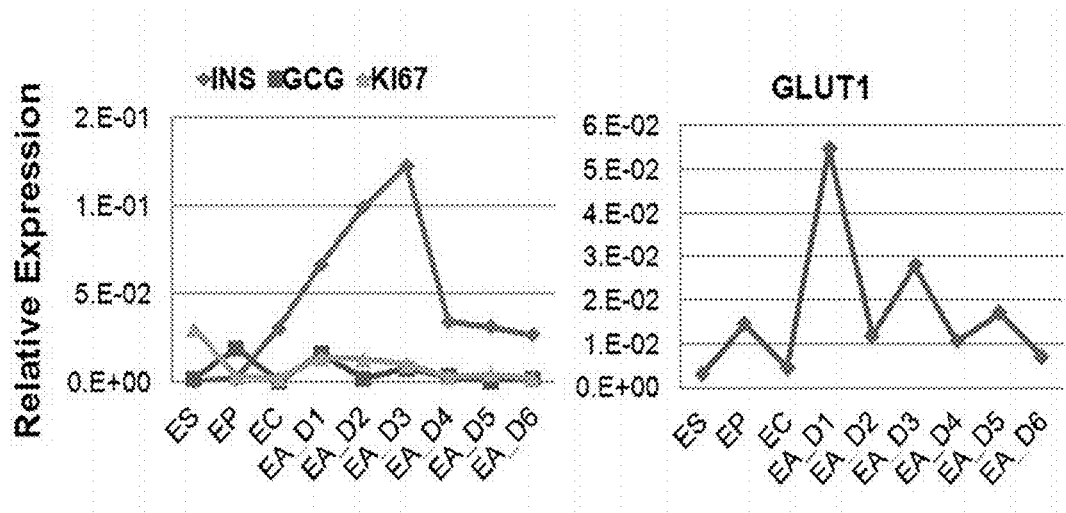
FIG. 5d is a diagram illustrating that the growth possibility of the endocrine aggregate generated from human embryonic stem cells was confirmed by using K167, the proliferation index, and the increase of the glucose transporter GLUT1 gene expression was also confirmed.
Figure 5E:
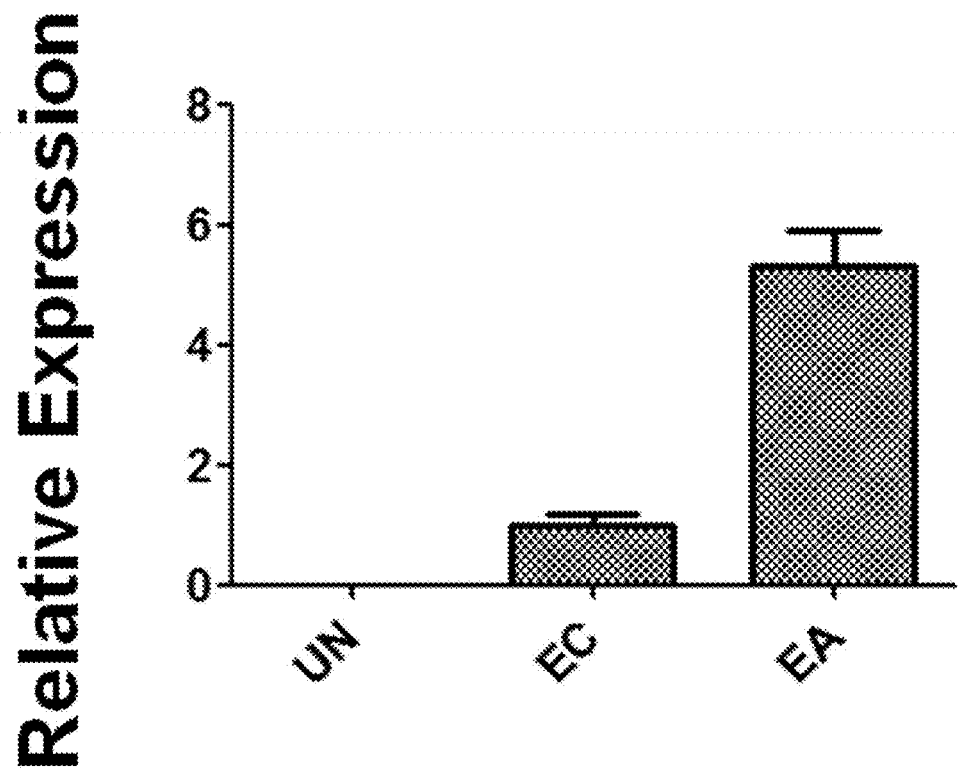
FIG. 5e is a diagram illustrating the increase of transcriptional expression of insulin from the endocrine aggregate differentiated from human embryonic stem cells, compared with that of endocrine cells.

As shown in FIG. 5d and FIG. 5e, the growth possibility of the endocrine aggregate generated from human embryonic stem cells was confirmed by using the proliferation index K167. It was also confirmed that the expression of the glucose transporter GLUT1 was significantly increased (FIG. 5d). From the comparison with the endocrine cells, it was confirmed that the transcriptional expression of insulin in the endocrine aggregate was significantly increased, suggesting that the aggregate had a functionally significant effect (FIG. 5e).

<5-3> Inducement and Confirmation of the Endocrine Aggregate from Endocrine Cells Originated from Human Induced Pluripotent Stem Cells To generate the endocrine aggregate from the endocrine cells originated from human induced pluripotent stem cells, the potential for aggregate formation and proliferation of the endocrine cells differentiated from human induced pluripotent stem cells in Example 4 was investigated.

Particularly, the formation of the endocrine aggregate was induced, by the same manner as described in Example <5-1>, from the endocrine cells differentiated from human induced pluripotent stem cells in Example 4 and then the growth possibility of the endocrine aggregate was investigated by the same manner as described in Example <5-2>.

Figure 6A:
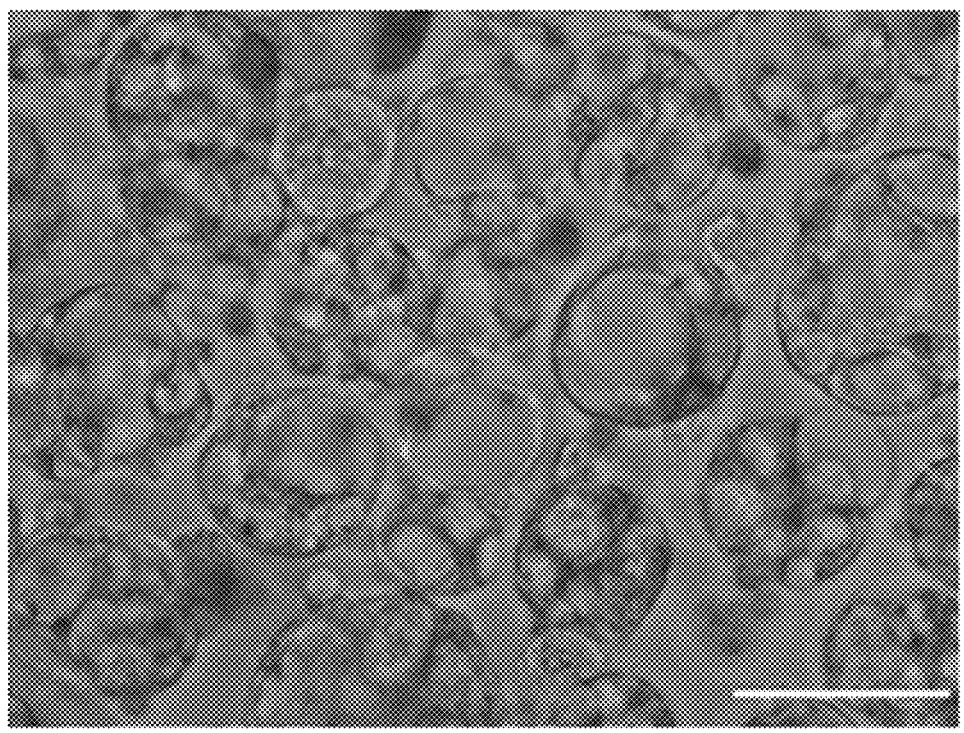
FIG. 6a is a diagram illustrating the endocrine aggregate generated from human embryonic stem cell-derived endocrine cells which was activated 24 hours later.
Figure 6B:
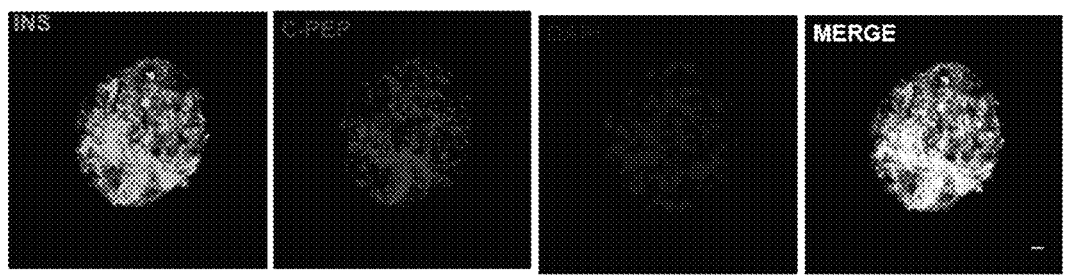
FIG. 6b is a diagram illustrating that the endocrine aggregate generated from human induced pluripotent stem cells was mostly composed of insulin expressing cells.
Figure 6C:
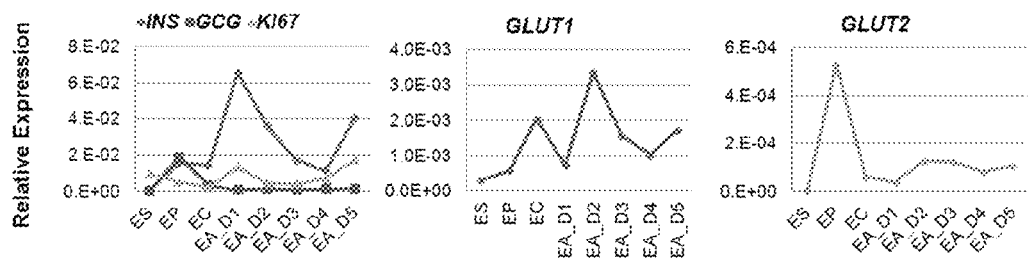
FIG. 6c is a diagram illustrating that the growth possibility of the endocrine aggregate generated from human induced pluripotent stem cells was confirmed by using K167, the proliferation index, and the increase of the glucose transporter GLUT1 gene expression was also confirmed.

As shown in FIG. 6a~FIG. 6c, the endocrine cells differentiated from not only human embryonic stem cells but also human induced pluripotent stem cells could form the endocrine aggregate which was activated 24 hours later (FIG. 6a). The endocrine aggregate was also composed mostly of insulin expressing cells (FIG. 6b). Like the endocrine aggregate generated from human embryonic stem cells, the endocrine aggregate formed from human induced pluripotent stem cells also had the growth potential, confirmed by using K167. In addition, it was confirmed that the expression of the glucose transporter GLUT1 gene was also increased therein (FIG. 6c).

Example 6: Confirmation of the In Vitro Function of Endocrine Aggregate (EA)

To investigate the in vitro functions of the insulin producing endocrine aggregate of Example 5, the pro-insulin C-peptide secretion was measured.

Particularly, insulin producing endocrine cells or the endocrine aggregate generated therefrom according to Example <5-1> were pre-cultured in KRBH (Krebs-Ringer bicarbonate with HEPES buffer) supplemented with 2.5 mM glucose at 37° C. for 1.5 hour. The composition of the said KRBH was as follows: 130 mM NaCl, 5 mM KCl, 1.25 mM $KH_2PO_4$, 1.25 mM $MgSO_4$, 2.68 mM $CaCl_2$, 5.26 mM $NaHCO_3$, 10 mM HEPES, and 0.1% BSA. Then, the cells were additionally cultured in KRBH supplemented with 27.7 mM glucose or 30 mM KCl at 37° C. for 1 hour. C-peptide secretion was measured by using C-peptide ELISA kit (Mercodia AB, Sweden). In addition, insulin and C-peptide were immunostained with the antibodies listed in Table 4 by the same manner as described in Example <2-1> to investigate the intracellular expressions of insulin and C-peptide.

Figure 5F:
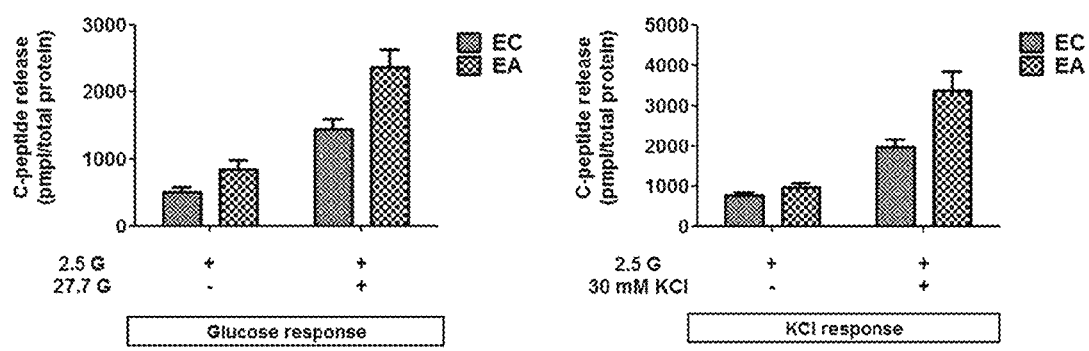
FIG. 5f is a diagram illustrating that the secretion of C-peptide, the pro-insulin, was increased by the stimulus of the high concentration of glucose or KCl in the endocrine aggregate differentiated from human embryonic stem cells.
Figure 5G:
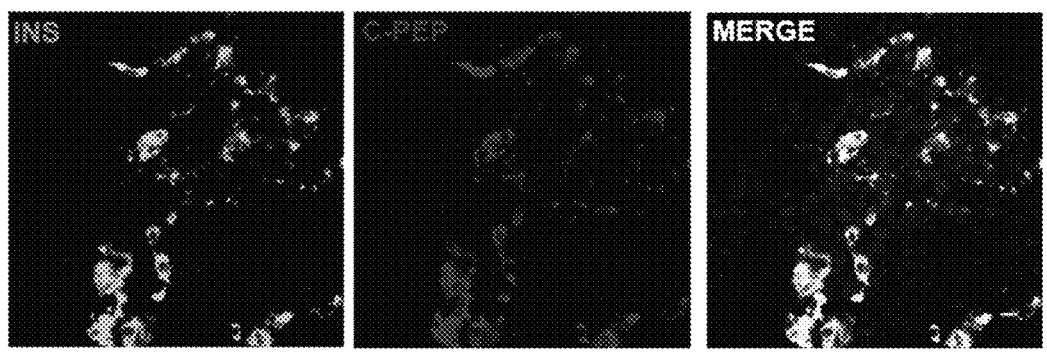
FIG. 5g is a diagram illustrating that the selective and efficient formation of the aggregate of insulin producing cells was achieved based on the fact that insulin producing cells spread on the monolayer were tend to form a cluster.
Figure 6D:
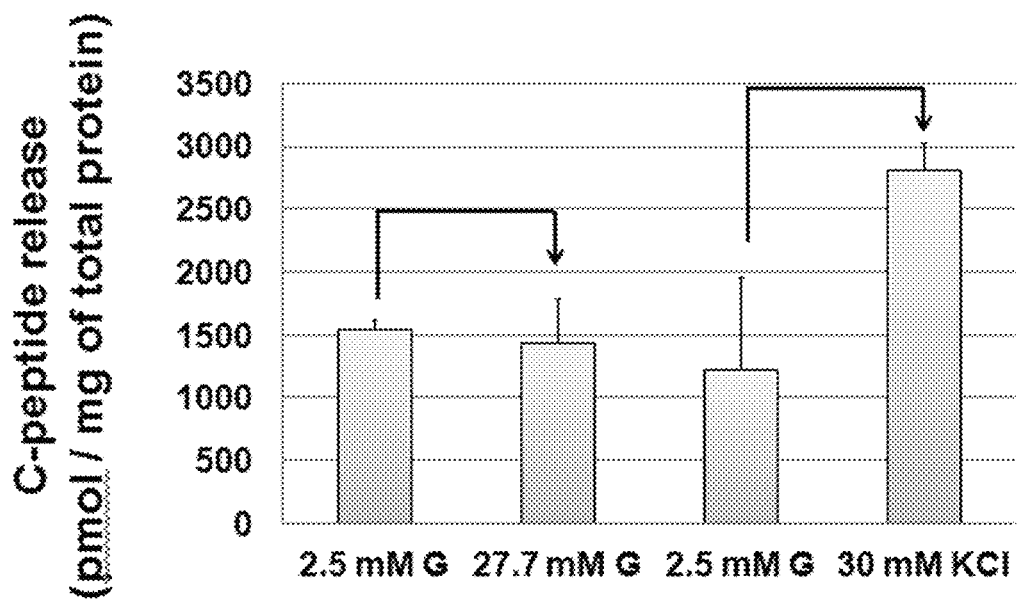
FIG. 6d is a diagram illustrating that the secretion of C-peptide, the pro-insulin, was increased by the stimulus of the high concentration of glucose or KCl in the endocrine aggregate differentiated from human induced pluripotent stem cells.

As a result, as shown in FIG. 5f, FIG. 5g, and FIG. 6d, it was confirmed that the secretion of the pro-insulin C-peptide was significantly increased in the endocrine aggregate generated from human embryonic stem cells by the stimulus of the high concentration of glucose or KCl (FIG. 5f). According to the tendency of the endocrine aggregate differentiated from human embryonic stem cells to form a cluster with insulin producing cells dispersed in the monolayer during the culture, insulin producing cell cluster was selectively and efficiently generated (FIG. 5g). It was also confirmed that the endocrine aggregate differentiated from human induced pluripotent stem cells secreted C-peptide, the pro-insulin, at a high level by responding to the high concentration of glucose or KCl (FIG. 6d).

Example 7: Confirmation of the In Vivo Function of Endocrine Aggregate (EA)

To investigate the in vivo functions of the insulin producing endocrine cells or the endocrine aggregate generated therefrom, those cells were transplanted in the test mouse, followed by performing glucose tolerance test.

Particularly, NOD.CB17-Prkdcscid/J mice at 4 weeks were obtained from KRRIB BEC (Korea). NOD.CB17-Prkdcscid/J mice at 5~10 weeks were raised with standard diet under 12 hr light/dark cycle. 4 days before the transplantation, 175 mg/kg of STZ (Streptozotocin, Sigma) was administered once by intraperitoneal injection to induce diabetes. Glucose level (blood glucose level) was measured every day before the transplantation and every 3 days after the transplantation by using a glucometer (Allmedicus Inc). Before the transplantation, 2.5% avertin (0.01 ml/g weight) was administered once by intraperitoneal injection to anesthetize the mouse. $6 \times 10^5$ cell-derived endocrine cells or $5 \times 10^4$ cell-derived endocrine aggregate was transplanted in the left kidney capsule. For the glucose tolerance test, the endocrine cells or the endocrine aggregate was transplanted in the diabetes induced mouse. One month later, the mouse was fasted for 16 hours during the night, and then glucose was injected intraperitoneally (2 g/kg weight), followed by measuring the blood glucose level. As the normal control, STZ non-treated group was used.

Figure 7B:
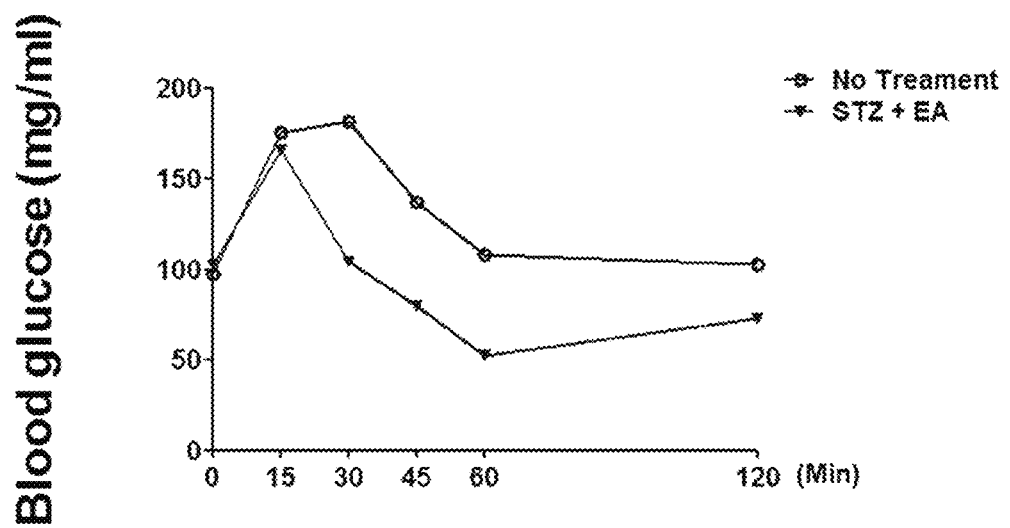
FIG. 7b is a graph illustrating that the endocrine aggregate transplanted in the mouse model with diabetes reduced the high concentration of glucose significantly almost to the normal level.

As a result, as shown in FIGS. 7a and 7b, when the endocrine aggregate was transplanted, the blood glucose was more efficiently regulated to maintain homeostasis than when the endocrine cells were transplanted (FIG. 7a). When the insulin producing endocrine aggregate was transplanted, the blood glucose was reduced significantly, compared with the normal control, suggesting that the aggregate could digest glucose significantly (FIG. 7b).

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for isolating an endocrine aggregate comprising insulin-producing β cells differentiated from human pluripotent stem cells, comprising the following steps:
   a) inducing differentiation of human pluripotent stem cells (hPSCs) into definitive endoderm (DE);
   b) inducing differentiation of the DE from step a) into pancreatic endoderm (PE);
   c) inducing differentiation of the PE from step b) into endocrine progenitors (EP);
   d) plating the EP from step c) onto a non-treated cell-culture plate or non-treated cell-culture dish and inducing differentiation of the EP into differentiated endocrine cells (EC), wherein the differentiated EC express increased levels of insulin, somatostatin (SST) and chromogranin A (CHA) as compared to insulin, SST and CHA levels during endocrine cell development in vivo, and the differentiated EC separates into a monolayer in suspension during culture in the cell-culture plate or dish and non-differentiated cells adhere to the non-treated cell-culture plate or dish;
   e) isolating the monolayer comprising the differentiated EC from step d) and producing an endocrine aggregate (EA) by 3D clustering; and
   f) isolating the EA from step e), wherein the EA comprises insulin-producing β cells.

2. The method for preparing the endocrine aggregate of insulin-producing β cells from human pluripotent stem cells according to claim 1, wherein the human pluripotent stem cells of step a) are human embryonic stem cells (hESCs) or human induced pluripotent stem cells (hiPSCs).

3. The method for preparing the endocrine aggregate of insulin-producing β cells from human pluripotent stem cells according to claim 1, wherein inducing the differentiation of human pluripotent stem cells (hPSCs) into definitive endoderm (DE) in step a) comprises culturing the human pluripotent stem cells in DMEM/F12 supplemented with Activin A, CHIR99021, and LiCl along with BSA or B27.

4. The method for preparing the endocrine aggregate of insulin-producing β cells from human pluripotent stem cells according to claim 1, wherein inducing the differentiation of definitive endoderm (DE) into pancreatic endoderm (PE) in step b) comprises culturing the definitive endoderm cells in DMEM supplemented with RA (retinoic acid), dorsomorphin (DM), SB431542, Activin A, bFGF (basic fibroblast growth factor), and Kaad-cyclopamine along with B27.

5. The method for preparing the endocrine aggregate of insulin-producing β cells from human pluripotent stem cells according to claim 1, wherein inducing the differentiation of pancreatic endoderm (PE) into endocrine progenitors (EP) in step c) comprises culturing the pancreatic endoderm cells in DMEM supplemented with dorsomorphin, SB431542, and DAPT along with B27 and ascorbic acid.

6. The method for preparing the endocrine aggregate of insulin-producing β cells from human pluripotent stem cells according to claim 1, wherein inducing the differentiation of endocrine progenitors (EP) into insulin producing endocrine cells (EC) in step d) comprises culturing the endocrine progenitors in CMRL supplemented with dbcAMP, Exendin-4, dorsomorphin, SB431542, and nicotinamide along with B27, ascorbic acid, and D-glucose.

7. An endocrine aggregate of insulin producing β cells prepared by the method of claim 1, wherein the β cells express increased levels of insulin, SST and CHA as compared to insulin, SST and CHA levels during endocrine cell development in vivo.

8. The endocrine aggregate of insulin-producing β cells according to claim 7, wherein secretion of C-peptide from the endocrine aggregate is increased upon stimulation from glucose or KCl.

9. The endocrine aggregate of insulin-producing β cells according to claim 7, wherein the endocrine aggregate regulates homeostasis of glucose when it is transplanted in a living body.

10. A method for proliferating insulin-producing cells comprising the step of culturing the endocrine aggregate of insulin-producing β cells of claim 7.

11. A pharmaceutical composition for the treatment of diabetes containing the endocrine aggregate of claim 7 as an active ingredient.

* * * * *

SEQUENCE LISTING

<160> NUMBER OF SEQ ID NOS: 32

<210> SEQ ID NO 1
<211> LENGTH: 20
<212> TYPE: DNA
<213> ORGANISM: Artificial Sequence
<220> FEATURE:
<223> OTHER INFORMATION: CXCR4 for forward primer

<400> SEQUENCE: 1
ggtggtctat gttggcgtct                                            20

<210> SEQ ID NO 2
<211> LENGTH: 20
<212> TYPE: DNA
<213> ORGANISM: Artificial Sequence
<220> FEATURE:
<223> OTHER INFORMATION: CXCR4 for reverse primer

<400> SEQUENCE: 2
tggagtgtga cagcttggag                                            20

<210> SEQ ID NO 3
<211> LENGTH: 20
<212> TYPE: DNA
<213> ORGANISM: Artificial Sequence
<220> FEATURE:
<223> OTHER INFORMATION: SOX17 for forward primer

<400> SEQUENCE: 3
cagaatccag acctgcacaa                                            20

<210> SEQ ID NO 4
<211> LENGTH: 19
<212> TYPE: DNA
<213> ORGANISM: Artificial Sequence
<220> FEATURE:
<223> OTHER INFORMATION: SOX17 for reverse primer

<400> SEQUENCE: 4
gcggccggta cttgtagtt                                             19

<210> SEQ ID NO 5
<211> LENGTH: 20
<212> TYPE: DNA
<213> ORGANISM: Artificial Sequence
<220> FEATURE:
<223> OTHER INFORMATION: GATA4 for forward primer

<400> SEQUENCE: 5
tccaaaccag aaaacggaag                                            20

<210> SEQ ID NO 6
<211> LENGTH: 20
<212> TYPE: DNA
<213> ORGANISM: Artificial Sequence
<220> FEATURE:
<223> OTHER INFORMATION: GATA4 for reverse primer

<400> SEQUENCE: 6
ctgtgcccgt agtgagatga                                            20

<210> SEQ ID NO 7
<211> LENGTH: 20
<212> TYPE: DNA
<213> ORGANISM: Artificial Sequence

```
<220> FEATURE:
<223> OTHER INFORMATION: FOXA2 for forward primer

<400> SEQUENCE: 7
aacaagatgc tgacgctgag                                                      20

<210> SEQ ID NO 8
<211> LENGTH: 20
<212> TYPE: DNA
<213> ORGANISM: Artificial Sequence
<220> FEATURE:
<223> OTHER INFORMATION: FOXA2 for reverse primer

<400> SEQUENCE: 8
caggaaacag tcgttgaagg                                                      20

<210> SEQ ID NO 9
<211> LENGTH: 20
<212> TYPE: DNA
<213> ORGANISM: Artificial Sequence
<220> FEATURE:
<223> OTHER INFORMATION: PDX1 for forward primer

<400> SEQUENCE: 9
gttccgaggt agaggctgtg                                                      20

<210> SEQ ID NO 10
<211> LENGTH: 20
<212> TYPE: DNA
<213> ORGANISM: Artificial Sequence
<220> FEATURE:
<223> OTHER INFORMATION: PDX1 for reverse primer

<400> SEQUENCE: 10
aacataaccc gagcacaagg                                                      20

<210> SEQ ID NO 11
<211> LENGTH: 20
<212> TYPE: DNA
<213> ORGANISM: Artificial Sequence
<220> FEATURE:
<223> OTHER INFORMATION: HNF1 for forward primer

<400> SEQUENCE: 11
agcccaccaa caagaagatg                                                      20

<210> SEQ ID NO 12
<211> LENGTH: 20
<212> TYPE: DNA
<213> ORGANISM: Artificial Sequence
<220> FEATURE:
<223> OTHER INFORMATION: HNF1 for reverse primer

<400> SEQUENCE: 12
cattctgccc tgttgcattc                                                      20

<210> SEQ ID NO 13
<211> LENGTH: 20
<212> TYPE: DNA
<213> ORGANISM: Artificial Sequence
<220> FEATURE:
<223> OTHER INFORMATION: HNF4 for forward primer

<400> SEQUENCE: 13
cgagcagatc cagttcatca                                                      20
```

```
<210> SEQ ID NO 14
<211> LENGTH: 20
<212> TYPE: DNA
<213> ORGANISM: Artificial Sequence
<220> FEATURE:
<223> OTHER INFORMATION: HNF4 for reverse primer

<400> SEQUENCE: 14
cgttggttcc catatgttcc                                              20

<210> SEQ ID NO 15
<211> LENGTH: 20
<212> TYPE: DNA
<213> ORGANISM: Artificial Sequence
<220> FEATURE:
<223> OTHER INFORMATION: SOX9 for forward primer

<400> SEQUENCE: 15
tacgactaca ccgaccacca                                              20

<210> SEQ ID NO 16
<211> LENGTH: 20
<212> TYPE: DNA
<213> ORGANISM: Artificial Sequence
<220> FEATURE:
<223> OTHER INFORMATION: SOX9 for reverse primer

<400> SEQUENCE: 16
tcaaggtcga gtgagctgtg                                              20

<210> SEQ ID NO 17
<211> LENGTH: 20
<212> TYPE: DNA
<213> ORGANISM: Artificial Sequence
<220> FEATURE:
<223> OTHER INFORMATION: HLXB9 for forward primer

<400> SEQUENCE: 17
gcaccagttc aagctcaaca                                              20

<210> SEQ ID NO 18
<211> LENGTH: 20
<212> TYPE: DNA
<213> ORGANISM: Artificial Sequence
<220> FEATURE:
<223> OTHER INFORMATION: HLXB9 for reverse primer

<400> SEQUENCE: 18 cttttttgctg cgtttccatt                                             20

<210> SEQ ID NO 19
<211> LENGTH: 19
<212> TYPE: DNA
<213> ORGANISM: Artificial Sequence
<220> FEATURE:
<223> OTHER INFORMATION: INS for forward primer

<400> SEQUENCE: 19
ccagccgcag cctttgtga                                               19

<210> SEQ ID NO 20
<211> LENGTH: 23
<212> TYPE: DNA
<213> ORGANISM: Artificial Sequence
<220> FEATURE:
<223> OTHER INFORMATION: INS for reverse primer
```

```
<400> SEQUENCE: 20
ggttcaaggg ctttattcca tct                                          23

<210> SEQ ID NO 21
<211> LENGTH: 19
<212> TYPE: DNA
<213> ORGANISM: Artificial Sequence
<220> FEATURE:
<223> OTHER INFORMATION: GCG for forward primer

<400> SEQUENCE: 21
aggcagaccc actcagtga                                               19

<210> SEQ ID NO 22
<211> LENGTH: 20
<212> TYPE: DNA
<213> ORGANISM: Artificial Sequence
<220> FEATURE:
<223> OTHER INFORMATION: GCG for reverse primer

<400> SEQUENCE: 22
aacaatggcg acctcttctg                                              20

<210> SEQ ID NO 23
<211> LENGTH: 20
<212> TYPE: DNA
<213> ORGANISM: Artificial Sequence
<220> FEATURE:
<223> OTHER INFORMATION: SST for forward primer

<400> SEQUENCE: 23
ccccagactc cgtcagtttc                                              20

<210> SEQ ID NO 24
<211> LENGTH: 19
<212> TYPE: DNA
<213> ORGANISM: Artificial Sequence
<220> FEATURE:
<223> OTHER INFORMATION: SST for reverse primer

<400> SEQUENCE: 24
tccgtctggt tgggttcag                                               19

<210> SEQ ID NO 25
<211> LENGTH: 20
<212> TYPE: DNA
<213> ORGANISM: Artificial Sequence
<220> FEATURE:
<223> OTHER INFORMATION: CHGA for forward primer

<400> SEQUENCE: 25
cctgtcagcc aggaatgttt                                              20

<210> SEQ ID NO 26
<211> LENGTH: 20
<212> TYPE: DNA
<213> ORGANISM: Artificial Sequence
<220> FEATURE:
<223> OTHER INFORMATION: CHGA for reverse primer

<400> SEQUENCE: 26
catccttgga tgatggctct                                              20

<210> SEQ ID NO 27
```

```
<211> LENGTH: 20
<212> TYPE: DNA
<213> ORGANISM: Artificial Sequence
<220> FEATURE:
<223> OTHER INFORMATION: PAS6 for forward primer

<400> SEQUENCE: 27
tgtgtgctct gaaggtcagg                                                 20

<210> SEQ ID NO 28
<211> LENGTH: 20
<212> TYPE: DNA
<213> ORGANISM: Artificial Sequence
<220> FEATURE:
<223> OTHER INFORMATION: PAS6 for reverse primer

<400> SEQUENCE: 28
ctggagctct gtttggaagg                                                 20

<210> SEQ ID NO 29
<211> LENGTH: 20
<212> TYPE: DNA
<213> ORGANISM: Artificial Sequence
<220> FEATURE:
<223> OTHER INFORMATION: GLUT1 for forward primer

<400> SEQUENCE: 29
gcaacggctt agacttcgac                                                 20

<210> SEQ ID NO 30
<211> LENGTH: 20
<212> TYPE: DNA
<213> ORGANISM: Artificial Sequence
<220> FEATURE:
<223> OTHER INFORMATION: GLUT1 for reverse primer

<400> SEQUENCE: 30
tgcgacttca ggcacataac                                                 20

<210> SEQ ID NO 31
<211> LENGTH: 19
<212> TYPE: DNA
<213> ORGANISM: Artificial Sequence
<220> FEATURE:
<223> OTHER INFORMATION: KI67 for forward primer

<400> SEQUENCE: 31
ctttgggtgc gacttgacg                                                  19

<210> SEQ ID NO 32
<211> LENGTH: 18
<212> TYPE: DNA
<213> ORGANISM: Artificial Sequence
<220> FEATURE:
<223> OTHER INFORMATION: KI67 for reverse primer

<400> SEQUENCE: 32
gtcgaccccg ctcctttt                                                   18
```